(12) United States Patent
Kuroda et al.

(10) Patent No.: US 8,372,607 B2
(45) Date of Patent: Feb. 12, 2013

(54) METHOD FOR PRODUCING SERINE DERIVATIVE AND PROTEIN USED FOR THE SAME

(75) Inventors: Shinji Kuroda, Kawasaki (JP); Masakazu Sugiyama, Kawasaki (JP); Kunihiko Watanabe, Kawasaki (JP); Shunichi Suzuki, Kawasaki (JP); Kenzo Yokozeki, Kawasaki (JP); Tatsuki Kashiwagi, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 189 days.

(21) Appl. No.: 12/836,984

(22) Filed: Jul. 15, 2010

(65) Prior Publication Data

US 2010/0317068 A1    Dec. 16, 2010

Related U.S. Application Data

(63) Continuation of application No. PCT/JP2009/050575, filed on Jan. 16, 2009.

(30) Foreign Application Priority Data

Jan. 18, 2008    (JP) ................. 2008-009853

(51) Int. Cl.
*C12P 13/06* (2006.01)
*C07H 21/00* (2006.01)
*C12N 1/21* (2006.01)
(52) U.S. Cl. .................. 435/116; 435/252.33; 536/23.2
(58) Field of Classification Search .................. None
See application file for complete search history.

(56) References Cited

U.S. PATENT DOCUMENTS

| | | | |
|---|---|---|---|
| 5,382,517 A | 1/1995 | Ura et al. | |
| 7,312,058 B2 | 12/2007 | Kashiwagi et al. | |
| 7,320,794 B2 | 1/2008 | Suzuki et al. | |
| 7,351,571 B2 | 4/2008 | Nakamatsu et al. | |
| 7,354,746 B1 | 4/2008 | Suzuki et al. | |
| 7,507,559 B2 | 3/2009 | Nozaki et al. | |
| 7,556,947 B2 | 7/2009 | Nozaki et al. | |
| 7,575,910 B2 | 8/2009 | Suzuki et al. | |
| 7,745,182 B2 | 6/2010 | Nozaki et al. | |
| 2006/0263861 A1 | 11/2006 | Nozaki et al. | |
| 2008/0241895 A1 | 10/2008 | Suzuki et al. | |
| 2009/0258398 A1 | 10/2009 | Nakamatsu et al. | |
| 2010/0143970 A1 | 6/2010 | Yokoyama et al. | |

FOREIGN PATENT DOCUMENTS

| | | |
|---|---|---|
| EP | 1882737 | 1/2008 |
| JP | 03-206892 | 9/1991 |
| JP | 07-327688 | 12/1995 |
| JP | 2006-320294 | 11/2006 |
| WO | WO2006/123745 | 11/2006 |

OTHER PUBLICATIONS

Nozaki, H., et al., "Cloning of the Gene Encoding α-Methylserine Hydroxymethyltransferase from *Aminobacter* sp. AJ110403 and *Ensifer* sp. AJ110404 and Characterization of the Recombinant Enzyme," Biosci. Biotechnol. Biochem. 2008;72(11):3002-3005.
Schirch, V., et al., "Serine hydroxymethyltransferase revisited," Curr. Op. Chem. Biol. 2005;9(5):482-487.
Supplementary European Search Report for EP Patent App. No. 09701789 (Jun. 9, 2011).
International Search Report and Written Opinion for PCT Patent App. No. PCT/JP2009/050575 (Mar. 3, 2009).

*Primary Examiner* — Tekchand Saidha
*Assistant Examiner* — Md. Younus Meah
(74) *Attorney, Agent, or Firm* — Shelly Guest Cermak; Cermak Nakajima LLP

(57) ABSTRACT

The present invention describes a method for generating a serine derivative and an optically active isomer thereof by a convenient technique, and an enzyme and the like useful in the method. In the presence of the following protein (A) and/or (B) having an enzymatic activity, an α-amino acid is reacted with an aldehyde to form a serine derivative:
(A) a protein comprising the amino acid sequence of SEQ ID NO:5, and
(B) a protein comprising an amino acid sequence of SEQ ID NO: 5, but which includes substitution, deletion, insertion and addition of one or more amino acids and is able to catalyze the reaction to form the serine derivative.

12 Claims, 1 Drawing Sheet

METHOD FOR PRODUCING SERINE DERIVATIVE AND PROTEIN USED FOR THE SAME

This application is a continuation under 35 U.S.C. §120 of PCT Patent Application No. PCT/JP2009/050575, filed Jan. 16, 2009, which claims priority under 35 U.S.C. §119 to Japanese Patent Application No. 2008-009853, filed on Jan. 18, 2008, which is incorporated in their entireties by reference. The Sequence Listing in electronic format filed herewith is also hereby incorporated by reference in its entirety (File Name: 2010-07-15T_US-433_Seq_List; File Size: 12 KB; Date Created: Jul. 15, 2010).

BACKGROUND OF THE INVENTION

1. Field of the Invention

The present invention relates to a method for producing a serine derivative. The present invention also relates to a protein having an enzymatic activity, which is used in the method for producing the serine derivative.

2. Brief Description of the Related Art

Serine derivatives, for example, amino acids having an optical activity at position α, such as β-hydroxy-α-L-amino acids, and β-hydroxy-α-D-amino acids, are expected to be useful as intermediates of pharmaceuticals. Thus, industrially advantageous methods for producing serine derivatives have been being developed.

Methods for producing serine derivatives using an enzyme have been disclosed, such as, for example, producing α-methyl-β-hydroxyphenylalanine using a microorganism belonging to the genus *Xanthomonas* (JP Hei-7-327688-A), and producing L-serine derivatives in an optically selective manner using microorganisms belonging to the genera *Ralstonia, Variovorax, Bosea* and *Silicibacter*, or a protein derived therefrom (International Publication WO2006/123745 Pamphlet).

SUMMARY OF THE INVENTION

As described above, various techniques have been studied regarding methods for producing optically active amino acids. However, there are many kinds of optically active amino acids and serine derivatives. Thus, more convenient techniques or more efficient methods for generating the various serine derivatives are required. It is an aspect of the present invention to provide a novel method for generating a serine derivative and optically active isomers thereof using a convenient technique, and an enzyme and the like used in the method.

A protein is disclosed that catalyzes a reaction in which an α-amino acid is reacted with an aldehyde. Furthermore, a serine derivative is formed using this protein. The following method is provided for producing the serine derivative, as well as the enzyme and the like used in the method.

It is an aspect of the present invention to provide a method for producing a serine derivative comprising reacting an α-amino acid of formula (I):

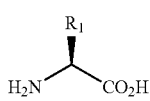

with an aldehyde of formula (II):

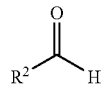

in the presence of an enzyme to form the serine derivative of formula (III):

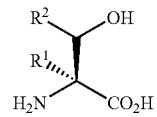

wherein $R^1$ is selected from the group consisting of an alkyl group having 1 to 7 carbon atoms, an aryl group having 6 to 14 carbon atoms, a cycloalkyl group having 3 to 10 carbon atoms, an aralkyl group having 7 to 19 carbon atoms, an alkoxyalkyl group having 2 to 11 carbon atoms, a group containing a hetero atom in the carbon skeleton thereof, and a group containing a carbon-carbon unsaturated bond in the carbon skeleton thereof, wherein these groups may be straight or branched, may have an alicyclic hydrocarbon structure and may further have a substituent, wherein $R^2$ is selected from the group consisting of hydrogen, an alkyl group having 1 to 7 carbon atoms, an aryl group having 6 to 14 carbon atoms, a cycloalkyl group having 3 to 10 carbon atoms, an aralkyl group having 7 to 19 carbon atoms, an alkoxyalkyl group having 2 to 11 carbon atoms, a group containing a hetero atom in the carbon skeleton thereof, and a group containing a carbon-carbon unsaturated bond in the carbon skeleton thereof, wherein these groups may be straight or branched, may have an alicyclic hydrocarbon structure and may further have a substituent;

wherein the enzyme is selected from the group consisting of:

(A) a protein comprising the amino acid sequence of SEQ ID NO:5, and (B) a protein comprising the amino acid sequence of SEQ ID NO:5, but which includes substitution, deletion, insertion, and addition of one or several amino acids, and wherein said protein is able to catalyze the reaction to form the serine derivative represented by formula (II).

It is a further aspect of the present invention to provide the method for producing the serine derivative as described above, wherein the protein (B) comprises a substitution of the tyrosine located at position 339 with an amino acid selected from the group consisting of serine, histidine, and asparagine.

It is a further aspect of the present invention to provide the method for producing the serine derivative as described above, wherein the protein (B) comprises a substitution of the asparagine located at position 19 with a serine.

It is a further aspect of the present invention to provide a method for producing a serine derivative comprising reacting an α-amino acid of formula (I) with an aldehyde of formula (II) in the presence of a protein to form the serine derivative of formula (III), wherein the protein is derived from a microorganism belonging to genus *Rhodococcus* and is able to catalyze a reaction in which the α-amino acid of formula (I) is reacted with the aldehyde of formula (II) to form the serine derivative of formula (III).

It is a further aspect of the present invention to provide the method for producing the serine derivative as described above, wherein the microorganism, the α-amino acid of formula (I) and the aldehyde of formula (II) are mixed to form the serine derivative of formula (III).

It is a further aspect of the present invention to provide the method for producing the serine derivative as described above, wherein a culture comprising the microorganism, the α-amino acid of formula (I) and the aldehyde of formula (II) are mixed to form the serine derivative of formula (III).

It is a further aspect of the present invention to provide the method for producing the serine derivative as described above, wherein the microorganism is treated to produce a microbial cell product, and the microbial cell product, the α-amino acid of formula (I), and the aldehyde of formula (II) are mixed to form the serine derivative of formula (III).

It is a further aspect of the present invention to provide the method for producing the serine derivative as described above, wherein the amino acid of formula (I) is selected from the group consisting of phenylalanine, leucine, methionine, alanine, cysteine, tryptophan, isoleucine, cyclohexylalanine, 2-amino-n-butyric acid, 2-aminovaleric acid, 2-aminohexanoic acid, and combinations thereof.

It is a further aspect of the present invention to provide the method for producing the serine derivative as described above, wherein the amino acid of formula (I) is α-phenylalanine and the serine derivative of formula (III) is α-benzylserine.

It is a further aspect of the present invention to provide the method for producing the serine derivative as described above, wherein the amino acid of formula (I) is α-leucine and the serine derivative of formula (III) is α-isobutylserine.

It is a further aspect of the present invention to provide the method for producing the serine derivative as described above, wherein the amino acid of formula (I) is α-methionine and the serine derivative of formula (III) is α-methylthioethylserine.

It is a further aspect of the present invention to provide a protein which is derived from a microorganism belonging to genus *Rhodococcus* and is able to catalyze a reaction in which an α-amino acid of formula (I) is reacted with an aldehyde of formula (II) to form a serine derivative of formula (III).

It is a further aspect of the present invention to provide a proteins selected from the group consisting:

(A) a protein comprising the amino acid sequence of SEQ ID NO:5, and (B) a protein comprising the amino acid sequence of SEQ ID NO: 5, but which includes substitution, deletion, insertion, and addition of one or several amino acids, wherein the protein is able to catalyze a reaction in which an α-amino acid of formula (I) is reacted with an aldehyde of formula (II) to form a serine derivative of formula (III).

It is a further aspect of the present invention to provide the protein as described above, wherein the protein (B) comprises a substitution of the tyrosine located at position 339 with an amino acid selected from the group consisting of serine, histidine, and asparagine.

It is a further aspect of the present invention to provide the protein as described above, wherein the protein (B) comprises a substitution of the asparagine located at position 19 with a serine.

It is a further aspect of the present invention to provide a polynucleotide encoding the protein as described above.

It is a further aspect of the present invention to provide a polynucleotide selected from the group consisting:

(a) a polynucleotide comprising the nucleotide sequence of SEQ ID NO:4, and (b) a polynucleotide that hybridizes with a polynucleotide having a nucleotide sequence complementary to the nucleotide sequence of SEQ ID NO:4 under stringent conditions and encodes a protein which is able to catalyze a reaction in which an α-amino acid of formula (I) is reacted with an aldehyde of formula (II) to form a serine derivative of formula (III).

It is a further aspect of the present invention to provide a cell transformed with the polynucleotide as described above.

It is a further aspect of the present invention to provide the cell as described above, which is *Escherichia coli*.

According to the present invention, it is possible to produce various serine derivatives by the reaction system as described herein.

DESCRIPTION OF THE PREFERRED EMBODIMENTS

Embodiments of the present invention will be described below together with best modes thereof.

Standard experiment manuals, such as Molecular Cloning: A Laboratory Manual, 3rd edition, Cold Spring Harbor Press (2001) and New Gene Engineering Handbook, revised 4th edition edited by Muramatsu et al., Yodosha (2003), can be referenced for various genetic engineering techniques, and those skilled in the art can perform these techniques with reference to these manuals. Unless otherwise specified herein, a sequence ID number indicates a sequence ID number in the Sequence Listing. An enzyme can refer to a protein which is able to catalyze a chemical reaction.

Figure 1:
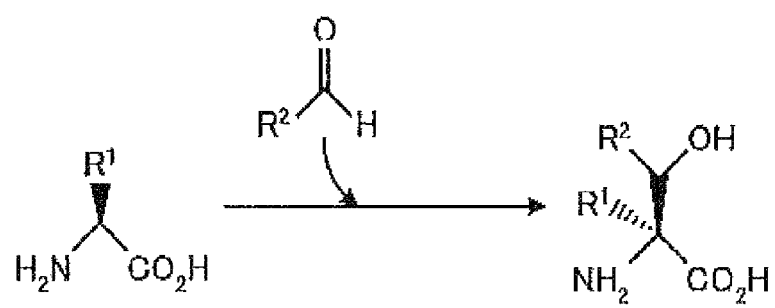
FIG. 1 shows the reaction of an α-amino acid with an aldehyde to form a serine derivative.

The method for producing serine derivatives in accordance with the presently disclosed subject matter utilizes an enzyme as a catalyst, and a reaction system in which an α-amino acid of formula (I) is reacted with an aldehyde of formula (II), resulting in a compound of formula (III) (FIG. 1).

In reference to FIG. 1, $R^1$ can be an alkyl group having 1 to 7 carbon atoms, which can include, for example, a methyl, ethyl, n-propyl, isopropyl, n-butyl, isobutyl, sec-butyl, tert-butyl, n-pentyl, isopentyl, neopentyl, n-hexyl, or isohexyl group. Specific examples of an alkyl group having an alicyclic hydrocarbon structure in the carbon skeleton can include cyclohexylmethyl.

$R^1$ can be an aryl group having 6 to 14 carbon atoms, which can include, for example, a phenyl, tolyl, xylyl, biphenyl, naphthyl, anthryl, or phenanthryl group.

$R^1$ can be a cycloalkyl group having 3 to 10 carbon atoms, which can include, for example, a cyclopropyl, cyclobutyl, cyclopentyl, cyclohexyl, cycloheptanyl, cyclooctanyl, cyclononanyl, or cyclodecanyl.

$R^1$ can be an aralkyl group having 7 to 19 carbon atoms, which can include, for example, a phenylalkyl such as benzyl, benzhydryl, phenethyl and a trityl, and cinnamyl, styryl, or naphthylalkyl group.

$R^1$ can be an alkoxyalkyl group having 2 to 11 carbon atoms, which can include, for example, an alkyl group having 1 to 10 carbon atoms substituted with a group such as, for example, a methoxy, ethoxy, propoxy, isopropoxy, butoxy, pentyloxy, phenoxy, heptoxy, octoxy, nonanoxy, decanoxy, or undecoxy substituent.

$R^1$ can be a group which includes a hetero atom in the carbon skeleton of the hydrocarbon. The heteroatom can include oxygen, nitrogen, or sulfur.

$R^1$ can be a heterocycle-containing hydrocarbon group. The heterocycle-containing hydrocarbon group is a cyclic hydrocarbon group which includes a hetero atom in the ring of a cyclic compound. The heterocycle-containing hydrocarbon group can include a heteroaryl, is not limited to the presence or absence of an aromatic property, and may be monocyclic or polycyclic. Heterocycle-containing hydrocarbon groups include, for example, a furyl, thienyl, pyridyl, piperidil, piperidino, morpholino, indolyl, or imidazolyl group, and alkyl groups substituted with these heterocyclic groups.

$R^1$ can be a hydrocarbon group which includes a carbon-carbon unsaturated bond in the carbon skeleton thereof in the groups shown above.

Furthermore, $R^1$ can be straight or branched. $R^1$ can also have an alicyclic hydrocarbon structure in the carbon skeleton thereof. The alicyclic hydrocarbon structure can include substituent structures, such as cyclopropane, cyclobutane, cyclopentane and cyclohexane, in which one or more hydrogen groups have been removed from the carbon skeleton.

$R^1$ can be the hydrocarbon group as described above, substituted with and/or adding of one or more halogen atoms, an alkyl group having up to 3 carbon atoms, an alkoxyl group having up to 3 carbon atoms, and a keto ($=$O), hydroxyl (—OH), thiol (—SH), amino (—$NH_2$), amide (—$CONH_2$), imino (=NH), or hydrazino (—$NHNH_2$) group.

Examples of the α-amino acid shown in formula (I) can include alanine, valine, leucine, isoleucine, serine, threonine, cysteine, methionine, asparagine, glutamine, phenylalanine, tyrosine, tryptophan, aspartic acid, glutamic acid, lysine, arginine, histidine, 2-amino-n-butyric acid, cyclohexylalanine, 2-aminovaleric acid (norvaline), and 2-aminohexanoic acid (norleucine), which are all α-types.

In reference to FIG. 1, $R^2$ may be hydrogen.

$R^2$ can be an alkyl group having 1 to 7 carbon atoms, which can include, for example, a methyl, ethyl, n-propyl, isopropyl, n-butyl, isobutyl, sec-butyl, tert-butyl, n-pentyl, isopentyl, neopentyl, n-hexyl, or isohexyl group. Specific examples of the alkyl group having an alicyclic hydrocarbon structure in the carbon skeleton thereof can include, for example, cyclohexylmethyl.

$R^2$ can be an aryl group having 6 to 14 carbon atoms, which can include, for example, a phenyl, tolyl, xylyl, biphenyl, naphthyl, anthryl, or phenanthryl group.

$R^2$ can be a cycloalkyl group having 3 to 10 carbon atoms, which can include, for example, a cyclopropyl, cyclobutyl, cyclopentyl, cyclohexyl, cycloheptanyl, cyclooctanyl, cyclononanyl, or cyclodecanyl group.

$R^2$ can be an aralkyl group having 7 to 19 carbon atoms, which can include, for example, a phenylalkyl such as benzyl, benzhydryl, phenethyl and trityl, and a cinnamyl, styryl, or naphthylalkyl group.

$R^2$ can be an alkoxyalkyl having 2 to 11 carbon atoms, which can include, for example, an alkyl group having 1 to 10 carbon atoms substituted with a group such as methoxy, ethoxy, propoxy, isopropoxy, butoxy, pentyloxy, phenoxy, heptoxy, octoxy, nonanoxy, decanoxy, or undecoxy.

$R^2$ can be a group which includes a hetero atom in the carbon skeleton of the above hydrocarbon. The hetero atom can include oxygen, nitrogen, or sulfur.

$R^2$ can be a heterocycle-containing hydrocarbon group. The heterocycle-containing hydrocarbon group includes a cyclic hydrocarbon group which includes a hetero atom in the ring of the cyclic compound. The heterocycle-containing hydrocarbon group can include heteroaryl, is not limited to the presence or absence of an aromatic property, and may be monocyclic or polycyclic. Heterocycle-containing hydrocarbon groups include, for example, a furyl, thienyl, pyridyl, piperidil, piperidino, morpholino, indolyl or imidazolyl group, and alkyl groups substituted with these heterocyclic groups.

$R^2$ can be the hydrocarbon group which includes a carbon-carbon unsaturated bond in the carbon skeleton thereof in the groups shown above.

Furthermore, $R^2$ can be straight or branched. $R^2$ can also have an alicyclic hydrocarbon structure in the carbon skeleton thereof. The alicyclic hydrocarbon structure can include substituent structures such as cyclopropane, cyclobutane, cyclopentane and cyclohexane, in which one or more hydrogen groups have been removed from the carbon skeleton.

$R^2$ can be the hydrocarbon group as described above, substituted with and/or adding of one or more halogen atoms, an alkyl group having up to 3 carbon atoms, an alkoxyl group having up to 3 carbon atoms, and a keto ($=$O), hydroxyl (—OH), thiol (—SH), amino (—$NH_2$), amide (—$CONH_2$), imino (=NH), or hydrazino (—$NHNH_2$) group.

Examples of the compound of formula (II) can include formaldehyde and acetaldehyde.

$R^1$ and $R^2$ of formula (III) are the same as the $R^1$ and $R^2$ of formula (I) and formula (II).

Figure 2:
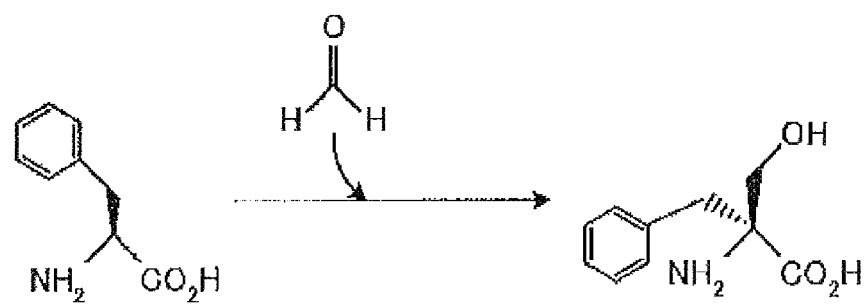
FIG. 2 shows one embodiment of the reaction system for producing various serine derivatives.

A reaction system is described in which L-α-phenylalanine is reacted with formaldehyde to form α-benzyl-L-serine as shown in FIG. 2. As exemplified in FIG. 2, formaldehyde in this reaction system is directly reacted with L-amino acid to form the L-serine derivative, and it is unnecessary to pass through 5,10-methylene tetrahydrofolate. As described above, the L-serine derivative can be obtained in the simple reaction system. Formaldehyde can be added in small portions sequentially. By adding formaldehyde sequentially, the generation of byproducts and the like is inhibited.

Other systems include those in which L-leucine is reacted with formaldehyde to form α-isobutyl-serine, and L-methionine is reacted with formaldehyde to form α-methylthioethyl-serine.

The reaction temperature can be 10 to 60° C., and in another example, 20 to 40° C. The pH value in the reaction system can be 4 to 10, and in another example, 6 to 9.

The serine derivative can be isolated from the enzyme reaction solution after the reaction is completed, for example, as follows.

The enzyme reaction solution is sterilized by heating, and then the pH is lowered, and dissolved proteins are agglutinated. Subsequently, bacteria and the proteins are removed by centrifugation, filtration, or UF (ultrafiltration). Inorganic salts are present in this solution. Thus, desalting is performed in order to prevent precipitation upon crystallization. The desalting may be performed by any of NF (nanofiltration), electric dialysis, ion exchange resin, and the like.

After performing the above desalting as needed, the reaction solution is concentrated, and a crystal of the L-serine derivative is precipitated. The crystal is fine, and upon separation by crystallization, a high yield is not obtained due to its high solubility. Additionally, handling of the crystal can be difficult due to its high viscosity. Thus, the crystallization can be performed by adding a poor solvent after preliminarily concentrating the solution as needed. The preliminary concentration can be performed until the crystal begins to precipitate. The poor solvent can be a lower alcohol and acetone that are water-soluble. By cooling the crystallization product after the crystallization with a poor solvent, it is also possible to increase the crystallization rate. The crystal of the L-serine derivative can be obtained by separating this slurry and drying the wet cake.

The reaction of an aldehyde of formula (II) and an α-amino acid is performed in the presence of an enzyme. The enzyme that is able to catalyze this reaction can be obtained from, for example, a microorganism belonging to the genus *Rhodococcus*. *Rhodococcus* sp. and *Rhodococcus* sp. AJ110611 can be included. The *Rhodococcus* sp. AJ110611 strain was deposited at the following Authority Depository and given the accession number FERM BP-11042. The bacterial strain with this FERM number can be obtained with reference to this accession number.

Name: *Rhodococcus* sp. AJ110611
Accession number: FERM BP-11042
Authority Depository: Patent Microorganism Depository, National Institute of Advanced Industrial Science and Technology
Address of Authority Depository: 1-1-1 Central No. 6 Higashi, Tsukuba-shi, Ibaraki Prefecture, Japan
Deposit Date: Mar. 29, 2007

The accession number of FERM P-21281 was given to the *Rhodococcus* sp. AJ110611 strain on Mar. 29, 2007, but the accession number of FERM BP-11042 was assigned after a procedural transfer within the Depository.

*Rhodococcus* sp. AJ110611 strain was initially deposited as *Rhodococcus percolatus* AJ110611 on Mar. 29, 2007, but as a result of its subsequent re-identification, it was determined that this microorganism should be classified as *Rhodococcus* sp. Thus, its name was changed to *Rhodococcus* sp. AJ110611 strain in the above authority depository, but only its name was changed. The microorganism itself was not changed.

More specifically, the following proteins are examples of the enzyme which can catalyze the reaction to form the serine derivatives:

(A) a protein having the amino acid sequence of SEQ ID NO:5 (number of amino acid residues: 365)

(B) a protein having the amino acid sequence of SEQ ID NO: 5, but wherein one or several amino acids can be substituted, deleted, inserted, and/or added, and wherein the protein is able to catalyze the reaction in which an α-amino acid of formula (I) is reacted with an aldehyde of formula (II) to form an serine derivative of formula (III).

By using this enzyme, the serine derivative can be easily and simply produced.

The enzyme of SEQ ID NO:5 can be isolated from, for example, *Rhodococcus* sp. (AJ110611 strain). The enzyme has broad substrate specificity as demonstrated by following Examples.

A protein that is substantially the same as the protein of SEQ ID NO: 5 can be used, such as that described in (B) above. The term "one or several amino acids" indicates a range of the amino acid residues wherein the three dimensional structure and the activity of a protein are not significantly impaired although it can vary depending on the position and the mutation type in the three dimensional structure of the protein. The term "one or several amino acids" can indicate, for example, 1 to 100, or in another example, 1 to 70, or in another example, 1 to 40, or in another example, 1 to 20, or in another example, 1 to 10, or in another example, 1 to 5 amino acids. In this regard, however, the enzyme with the above-described changes can retain the enzymatic activity at about a half or more, or in another example, 80% or more, or in another example, 90%, or in another example, 95% or more of the protein having the amino acid sequence of SEQ ID NO:5 at 30° C. at pH 7 to 8.

The protein described in (B) above can be obtained by modifying the nucleotide sequence by site-directed mutagenesis such that the amino acid corresponding to a particular position in the gene encoding the protein is substituted, deleted, inserted, added or the like. A polynucleotide having the modified nucleotide sequence as above can be obtained by conventionally known mutagenesis techniques. Examples of these mutagenesis techniques can include treating the DNA encoding the protein (A) with hydroxylamine and the like in vitro, and treating bacteria of genus *Escherichia* having the DNA encoding the protein (A) with a mutagenic agent such as an ultraviolet ray, or N-methyl-N'-nitro-N-nitrosoguanidine (NTG) or nitrous acid, which are known agents for artificial mutagenesis.

The substitution, deletion, insertion and addition can include differences due to species and the strain of the microorganisms, and naturally occurring mutations. DNA encoding substantially the same protein as the protein (A) is obtained by expressing the DNA having the mutation as above in an appropriate cell and examining the enzymatic activity in an expressed product.

A protein having an amino acid sequence that has 60% or more, or in another example, 70% or more, or in another example, 80% or more, or in another example, 90% or more, or in another example, 95% or more, or in another example, 98% or more homology to the amino acid sequence of the protein (A) is an example of a protein which is substantially the same as the protein (A). The homology of the amino acid sequences can be calculated using the GENETYX Ver7.0.9 software (supplied from Genetyx Corporation) with the setting at "unit size to compare=2" and using full length polypeptide chains encoded in the ORF, or calculated by a similar method wherein matches are counted on a percentage basis.

Examples of the above protein (B) can include the following mutant proteins:

(B1) a protein having the amino acid sequence of SEQ ID NO:5, but in which the tyrosine at position 339 is substituted with serine, histidine or asparagine.

These mutant proteins have a higher activity than protein (A) of catalyzing the reaction in which the amino acid of formula (I) is reacted with the aldehyde of formula (II) to form the serine derivative of formula (III). The mutant protein with the amino acid sequence in which tyrosine at position 339 is substituted with serine has a particularly high activity. The substitution in the amino acid sequence is represented by an abbreviation of "the original amino acid/the position number of the mutation/the abbreviation of the substituted amino acid" in this order. For example, when the tyrosine at position 339 is substituted with serine, the abbreviation can be "Y339S". The one letter code, as shown here, or the three letter code, are academically acceptable for indicating the amino acid. The one letter code will be also used for other mutants.

Furthermore, the mutant protein can include the following protein:

(B2) a protein having the amino acid sequence of SEQ ID NO: 5, but in which the asparagine at position 19 is substituted with a serine.

The mutation in the protein (B2) is abbreviated as "N19S". The mutation N19S is also involved in catalysis of the reaction in which the amino acid of formula (I) is reacted with the aldehyde of formula (II) to form the serine derivative of formula (III).

Other mutant proteins can include those in which both the amino acid at position 339 and the amino acid at position 19 are mutated in the amino acid sequence of SEQ ID NO:5, such as the following:
(1) "Y339S" and "N19S"
(2) "Y339H" and "N19S"
(3) "Y339H" and "N19S"

The protein having both mutations of "Y339S" and "N19S" can exhibit particularly high enzymatic activity when the amino acid of formula (I) is alanine.

A polynucleotide encoding the above protein (A) is also described. Multiple nucleotide sequences can encode a particular amino acid sequence due to the degeneracy of genetic code. That is, the polynucleotide encoding the protein (A) can the polynucleotide (a) having the nucleotide sequence of SEQ ID NO:4.

The polynucleotide (a) encodes the protein (A) and can be isolated from the *Rhodococcus* sp. AJ110611 strain.

Examples of other polynucleotides can include those encoding the above proteins (B1), (B2) and the other mutant proteins with the combination mutations. The polynucleotides encoding the mutant proteins can have a nucleotide sequence in which the nucleotide which corresponds to the mutant amino acid is substituted in accordance with the codon table in the nucleotide sequence of SEQ ID NO:4. For example, in the case of the protein having the mutation of "Y339S", the nucleotide sequence "tac" at positions 1015 to 1017 can be substituted with a serine-encoding nucleotide sequence such as "tct" in the nucleotide sequence of SEQ ID NO:4.

Methods for isolation will be described. DNA having the nucleotide sequence of SEQ ID NO:4 can be obtained from chromosomal DNA or a DNA library of *Rhodococcus* sp. by PCR (polymerase chain reaction, see White, T. J. et al; Trends Genet., 5, 185 (1989)) or hybridization. Primers used for PCR can be designed based on an internal amino acid sequence determined based on the purified protein which is able to catalyze the reaction as described herein. The primers or probes for the hybridization can also be designed based on the nucleotide sequence of SEQ ID NO:4, or the primers can also be isolated using the probes. When primers having the sequences corresponding to a 5'-untranslated region and a 3'-untranslated region so as to sandwich a coding region are used in PCR, the full length coding region of the protein can be amplified.

For example, the primer can be synthesized using a DNA synthesizer model 380B supplied from Applied Biosystems by the phosphoamidite method (see Tetrahedron Letters (1981), 22, 1859). The PCR reaction can be performed, for example, using Gene Amp PCR System 9600 (supplied from PERKIN ELMER) or TaKaRa LA PCR in vitro Cloning Kit (supplied from Takara Bio) in accordance with the methods designated by the manufacturers.

A polynucleotide which is substantially the same as the above polynucleotide (a) can also be used. Examples can include the following polynucleotide (b):

(b) a polynucleotide that hybridizes with a polynucleotide having a nucleotide sequence complementary to the nucleotide sequence of SEQ ID NO:4 under stringent conditions, and encodes a protein which is able to catalyze the reaction in which the α-amino acid of formula (I) is reacted with the aldehyde of formula (II) to form the serine derivative of formula (III).

For example, a probe may be used for hybridization. The probe can be made based on the nucleotide sequence of SEQ ID NO:4 in accordance with standard methods. The probe is hybridized to the polynucleotide, and the objective polynucleotide can be isolated in accordance with standard methods. For example, a DNA probe can be prepared by amplifying the nucleotide sequence cloned in a plasmid or a phage vector, cutting out the nucleotide sequence which is to be used as the probe using restriction enzymes and extracting it. Restriction sites can be determined depending on the objective DNA. Once the polynucleotide hybridizes, then it can be amplified by PCR in accordance with standard methods.

The "stringent conditions" can refer to conditions where a so-called specific hybrid is formed, and a non-specific hybrid is not formed. Examples thereof can include when DNA sequences with high homology, e.g., DNA sequences having homology of 60% or more, or in another example, 70% or more, or in another example, 80% or more, or in another example, 90% or more, or in another example, 95% or more, or in another example, 98% or more hybridize, and DNA with lower homology does not hybridize. The homology (%) of the nucleotide sequences can be calculated using the entire ORF (including the termination codon) of each gene and using the GENETYX Ver7.0.9 software (supplied from Genetyx Corporation) with the setting at "unit size to compare=6" and "pick up location=1", or calculated by a similar method in which the matching nucleotides are counted on a percentage basis. Also, another example can hybridization at salt concentrations of 1×SSC and 0.1% SDS at 60° C., and or in another example, 0.1×SSC and 0.1 SDS at 65° C. These are typical washing conditions in Southern hybridization. When a stop codon is present in an internal region of the gene sequence and the activity is lost due to the mutation of the active center, such genes can be included as being able to hybridize under stringent conditions. However, such genes can be easily removed by ligating them to a commercially available expression vector, expressing them in an appropriate host and measuring the enzymatic activity of the expressed product by methods described later.

The enzyme encoded by polynucleotide (b) can retain enzymatic activity at about a half or more, or in another example, 80% or more, or in another example, 90% of the protein (A) at 30° C. at pH 8.

As long as the described enzyme is present in the reaction system in a state so that it can catalyze the reaction as above, the form in which it exists is not particularly limited. That is, the enzyme which is present when the reaction is performed can be a part of a culture of the microorganism which can produce the enzyme, or can be a part of a cultured microbial cell which has been separated from the culture, or can be a part of a treated microbial cell product. The culture of the microorganism includes the products which are present upon culturing the microorganism, such as the cultured microbial cells, the medium used for culturing the microorganism, substances produced by the cultured microorganism, and mixtures thereof. The cultured microbial cell can be washed. The treated microbial cell product can include products obtained by disrupting, lysing, and lyophilizing the microbial cells, a cell-free extract, and the crude protein obtained by further treating the microbial cells, and the purified protein obtained by further purification. A partially purified protein obtained by various purification methods, and an immobilized protein obtained by immobilizing the protein by covalent bonding, adsorption, or both can be used. Depending on the chosen microorganism, it can be lysed during cultivation in some cases. Thus, the culture supernatant can also contain the objective enzyme.

Subsequently, methods for producing the protein, and methods for making the transformant cells containing the protein will be described for above protein (A). However, the same methods can also be used for the other mutant proteins.

The transformant that expresses the above protein (A) can be made by making a recombinant polynucleotide in which the polynucleotide having any of the above nucleotide sequences is incorporated. For example, the transformant that expresses the protein (A) can be obtained by producing a recombinant DNA in which DNA having the nucleotide sequence shown in SEQ ID NO:4 is incorporated and introducing it into an appropriate host. Exemplary hosts include various prokaryotic cells including bacteria belonging to genus *Escherichia* such as *Escherichia coli* and the genus *Corynebacterium, Bacillus subtilis*, and various eukaryotic cells including *Saccharomyces cerevisiae, Pichia stipitis* and *Aspergillus oryzae*. The serine derivative can be produced inexpensively and conveniently on a large scale by these hosts.

Recombinant DNA having the nucleotide sequence of SEQ ID NO:4 can be prepared by inserting the DNA having that sequence into a vector that will be functional in the chosen host for expressing the objective protein. If the native promoter of the chosen host will work, then the native promoter can be used. If necessary, alternative exogenous promoters which are functional in the chosen host may be ligated to the DNA of SEQ ID NO:4 so that the protein is expressed under the control of that promoter.

Transformation methods for introducing the recombinant DNA into the host cell can include D. M. Morrison's method (Methods in Enzymology 68, 326 (1979)) or a method of increasing a permeability of DNA by treating a recipient bacterium with calcium chloride (Mandel, M. and Higa, A., J. Mol. Biol., 53, 159 (1970)).

When producing the objective protein on a large scale using recombinant DNA technology, inclusion bodies of the protein can be formed, in which the protein is aggregated in the transformant. The advantages of this method include the protection of the objective protein from digestion by proteases present in the microbial cells, and convenient purification of the objective protein by disruption of the microbial cells, followed by centrifugation. To obtain the active protein from the inclusion bodies, a series of manipulations such as solubilization and activity regeneration is required, and thus is more complicated than when directly producing the active protein. However, when a protein which affects microbial cell growth is produced on a large scale in the microbial cells, the effects thereof can be inhibited by production of the protein as an inactive inclusion body in the microbial cells.

To produce the objective protein on a large scale in inclusion bodies, expressing the protein alone under the control of a strong promoter, as well as expressing the objective protein as a fusion protein with a protein which is known to be expressed in a large amount is available.

A strain typically used to express exogenous genes can be used for the host, and can include subspecies of *Escherichia coli* K12, JM109, DH5α, HB101, and BL21 (DE3). Methods of performing the transformation and methods of selecting the transformant are also described in Molecular Cloning: A Laboratory Manual, 3rd edition, Cold Spring Harbor press (2001/01/15). Hereinafter, methods of transforming *Escherichia coli* and producing the objective enzyme will be more specifically described as one example.

Promotors typically used in the production of an xenogenous protein in *Escherichia coli* can be used to express the DNA encoding the protein having the catalytic activity. Examples thereof can include strong promoters such as T7 promoter, lac promoter, trp promoter, trc promoter, tac promoter, PR and PL promoters of lambda phage, and T5 promoter. As the vector, for example, pUC19, pUC18, pBR322, pHSG299, pHSG298, pHSG399, pHSG398, RSF1010, pACYC177, pACYC184, pMW119, pMW118, pMW219, pMW218, pQE30 and derivatives thereof can be used. As the other vector, a vector of phage DNA may be utilized. An expression vector that contains the promoter and can express an inserted DNA sequence can be used.

In order to produce the protein as a fusion protein inclusion body, a gene encoding another protein, such as a hydrophilic peptide, is ligated to an upstream or downstream of the protein. The gene encoding the other protein can be one which increases the amount of the fusion protein produced, and enhances solubility of the fusion protein after modification and regeneration. Examples include the T7 gene 10, β-galactosidase gene, dehydrofolate reductase gene, interferon γ gene, interleukin-2 gene, prochymosin gene, and the like.

These genes are ligated to the gene encoding the objective protein so that the reading frames of codons are matched. The ligation can be performed at an appropriate restriction enzyme sites, or by using synthetic DNA with an appropriate sequence.

In order to augment the amount produced, a transcription termination sequence, for example, a terminator, can be ligated downstream of the fusion protein gene. This terminator can include the T7 terminator, fd phage terminator, T4 terminator, a terminator of a tetracycline resistant gene, a terminator of an *Escherichia coli* trpA gene, or the like.

The vector which can be used to introduce the gene encoding the protein having the catalytic activity, or to introduce the fusion protein into *Escherichia coli*, can be a so-called multiple-copy type. Plasmids having a replication origin derived from ColE1, such as pUC type plasmids, pBR322 type plasmids or derivatives thereof can be included. The term "derivatives" can indicate when the plasmids are modified by substitution, deletion, insertion, addition and/or inversion of nucleotides. The modification can include modification by mutagenic treatments by mutagenic agents and UV irradiation, or natural mutations.

The vector can have a marker such as an ampicillin resistant gene so that the transformant can be selected. Expression vectors with strong promoters are commercially available, for example, pUC (supplied from Takara Bio Co., Ltd.), pPROK (supplied from Clontech), pKK233-2 (supplied from Clontech) and the like.

A DNA fragment obtained by ligating the promoter, the gene encoding the objective protein or the fusion protein of the objective protein, and optionally, the terminator, in this order, is ligated to the vector DNA to obtain the recombinant DNA.

This recombinant DNA is used to transform *Escherichia coli*, and cultivation of this *Escherichia coli* results in expression and production of the objective protein or the fusion protein thereof.

When expressing as the fusion protein, the fusion protein may be composed so that is able to cleave the objective protein therefrom using a restriction protease which recognizes a sequence of blood coagulation factor Xa, kallikrein or the like which is not present in the objective protein.

The production media can include the media typically used for culturing *Escherichia coli*, such as M9-casamino acid medium and LB medium. Culture conditions and production induction conditions may be appropriately selected depending on the types of the vector marker, the promoter, the host bacterium, and the like.

The objective protein or the fusion protein can be recovered by the following method. When the objective protein or the fusion protein thereof is solubilized in the microbial cells, the microbial cells can be collected and then disrupted or lysed, to obtain a crude enzyme solution. If necessary, the objective protein or the fusion protein thereof can further be purified in accordance with ordinary techniques such as precipitation, filtration and column chromatography. The purification can be utilized in accordance with methods utilizing an antibody against the objective protein or the fusion protein. When the protein inclusion body is formed, this is solubilized with a denaturing agent, and the objective protein can be obtained by removing the denaturing agent by dialysis and the like.

EXAMPLES

The present invention will be illustrated in more detail with reference to the following non-limiting Examples. *Rhodococcus* sp. AJ110611 strain used in the following Examples was designated as *Rhodococcus* percolatus AJ110611 strain on the deposit date of Mar. 29, 2007, but was subsequently re-identified as belonging to the class *Rhodococcus* sp., and will be referred to hereinafter as *Rhodococcus* sp. (AJ110611 strain).

Example 1

Detection of 2-Benzylserine Hydroxymethyltransferase Activity (Identification of Activity in Wild-Type Strain)

*Rhodococcus* sp. (AJ110611 strain) was cultured in an agar medium prepared with Nutrient Broth (Difco) at 30° C. for 24 hours. A liquid medium (pH 7.0) containing 3 mL of 0.2% α-benzyl-DL-serine and 0.17% Yeast Nitrogen Base without amino acid and ammonium sulfate (Difco) was inoculated with one loopful of cells of the cultured microorganism, and then cultured with shaking at 30° C. at 120 reciprocations/min for 24 hours. After the cultivation, the microbial cells were centrifuged, and washed twice with 50 mM potassium phosphate buffer (pH 7.4) containing 1 mL of 0.1 mM pyridoxal phosphate. A microbial cell suspension in a total amount of 0.3 ml was prepared using the washed microbial cells and 50 mM potassium phosphate buffer (pH 7.4) containing 0.1 mM pyridoxal phosphate. The resulting microbial cell suspension was sonicated and disrupted at 4° C. A supernatant obtained by centrifuging the microbial cell suspension after being sonicated was dialyzed against 50 mM potassium phosphate buffer (pH 7.4) containing 0.1 mM pyridoxal phosphate to make a cell-free extract solution.

A reaction mixture in a total amount of 0.1 mL obtained by adding 0.03 mL of the cell-free extract solution to a reaction solution A having a composition of 50 mM potassium phosphate buffer (pH 7.4), 10 mM α-benzyl-DL-serine and 0.1 mM pyridoxal phosphate was reacted at 30° C. for 10 minutes. After 10 minutes, the reaction was stopped by mixing 0.1 mL of an alkali reagent (5 N potassium hydroxide) attached in a formaldehyde kit, Test Wako (Wako Pure Chemicals Industries Ltd.).

Subsequently, a detection reaction of formaldehyde was performed and an absorbance at 550 nm was measured (E11) in accordance with the manual attached to the kit. As a control, the absorbance of a reaction solution obtained by the reaction using water instead of α-benzyl-DL-serine in the above reaction solution A was likewise measured (E10). An absorbance change (EΔ1=E11-E10) specific for α-benzyl-DL-serine was calculated from the measured values E11 and E10, and a value of 1.25 was obtained. From the above result, the 2-benzylserine hydroxymethyltransferase activity was confirmed in the cell-free extract solution prepared from *Rhodococcus* sp. (AJ110611 strain).

Example 2

Purification of 2-Benzylserine Hydroxymethyltransferase Derived from *Rhodococcus* sp. (AJ110611 strain)

(1) Preparation of Cell-Free Extract Solution

*Rhodococcus* sp. (AJ110611 strain) was cultured in the agar medium prepared with Nutrient Broth (Difco) at 30° C. for 24 hours. 50 mL of Nutrient Broth liquid medium in a 500 mL Sakaguchi flask was inoculated with cells of the cultured microorganism, and then cultured with shaking at 25° C. at 120 reciprocations/min for 19 hours. Twenty Sakaguchi flasks in which 50 mL of the liquid medium (pH 7.0) containing 0.2% α-benzyl-DL-serine and 0.17% Yeast Nitrogen Base without amino acid and ammonium sulfate (Difco) were prepared, and the liquid medium in the Sakaguchi flask was inoculated with 0.25 mL of the resulting culture medium. After the inoculation, the liquid medium was cultured with shaking at 25° C. at 120 reciprocations/min for 24 hours. The resulting microbial cells were collected by centrifugation (8,000×g, 10 minutes), and washed twice with 10 mL of 50 mM potassium phosphate buffer A (pH 7.4) containing 0.1 mM pyridoxal phosphate. The microbial cells were further washed twice with 25 mM potassium phosphate buffer B (pH 7.4) containing 0.02 mM pyridoxal phosphate and 1 mM EDTA to prepare 40 mL of a microbial cell suspension. The microbial cells were disrupted by sonication. A supernatant obtained by centrifugation (8,000×g, 20 minutes) was further subjected to ultracentrifugation (200,000×g, 30 minutes). The resulting supernatant was dialyzed against the potassium phosphate buffer B to obtain a cell-free extract solution.

(2) Anion-Exchange Chromatography

The cell-free extract solution obtained in (1) was applied to a Q-Sepharose-HP 16/10 column (supplied from Amersham Bioscience) previously equilibrated with the 25 mM potassium phosphate buffer B (pH 7.4) containing 0.02 mM pyridoxal phosphate and 1 mM EDTA, and the enzyme was eluted with a linear concentration gradient of 0 to 1 M sodium chloride. The enzymatic activity was measured in fractions suspected of containing the enzyme in accordance with the method in Example 1, and the activity of 2-benzylserine hydroxymethyltransferase was detected in the fractions corresponding to 0.3 to 0.4 M of sodium chloride.

(3) Hydrophobic Interaction Chromatography

The fraction having the enzymatic activity obtained in (2) was dialyzed against the 25 mM potassium phosphate buffer B (pH 7.4) containing 0.02 mM pyridoxal phosphate and 1 mM EDTA, and mixed with the buffer B containing an equal amount of 2 M ammonium sulfate. The resulting mixture was applied to a Phenyl-Sepharose-HP 16/10 column (supplied from Amersham Bioscience) previously equilibrated with the buffer B (pH 7.4) containing 1 M ammonium sulfate, and the enzyme was eluted with the linear concentration gradient of 1 to 0 M ammonium sulfate. The enzymatic activity was measured in fractions suspected of containing the enzyme in accordance with the method in Example 1, and the activity of 2-benzylserine hydroxymethyltransferase was detected in the fractions corresponding to 0.7 to 0.6 M ammonium sulfate.

(4) Gel Filtration Chromatography

The fraction having the enzymatic activity obtained in (3) was concentrated, applied to Superdex-200 16/60 column (supplied from Amersham Bioscience) previously equilibrated with the 25 mM potassium phosphate buffer (pH 7.4) containing 0.02 mM pyridoxal phosphate and 1 mM EDTA, and the enzyme was eluted. The enzymatic activity was measured using the obtained fractions in accordance with the method in Example 1, and the activity of 2-benzylserine hydroxymethyltransferase was detected in the fractions corresponding to 64 to 68 ml of the eluted volume.

(5) Anion-Exchange Chromatography

The fraction having the enzymatic activity obtained in (4) was applied to MonoQ HR5/5 column (supplied from Amersham Bioscience) previously equilibrated with the 25 mM potassium phosphate buffer (pH 7.4) containing 0.02 mM pyridoxal phosphate and 1 mM EDTA, and the enzyme was eluted with the linear concentration gradient of 0 to 0.7 M sodium chloride. The enzymatic activity was measured in fractions suspected of containing the enzyme in accordance with the method in Example 1, and the activity of 2-benzylserine hydroxymethyltransferase was detected in the fractions corresponding to 0.45 to 0.55 M of sodium chloride.

A specific activity in the active fraction of the enzyme obtained by passing through the above steps (1) to (5) was 1.82 U/mg. The resulting purified enzyme was subjected to SDS polyacrylamide electrophoresis and the gel was stained with SimplyBlue SafeStain (Invitrogen), and a uniform band was detected at a position corresponding to a molecular weight of about 40 kDa.

Example 3

Sequencing and Gene Cloning of 2-Benzylserine Hydroxymethyltransferase Derived from Rhodococcus Sp. (AJ110611 Strain)

100 pmol of the purified enzyme prepared in Example 2 was run on SDS-polyacrylamide electrophoresis, and then transferred to a PVDF membrane. The resulting sample was subjected to a protein sequencer PPSQ-21A supplied from Shimadzu Corporation, and the 23 amino acid residues at the N-terminus of the amino acid sequence were determined (SEQ ID NO:1).

Then, 5 μg of genomic DNA from Rhodococcus sp. (AJ110611 strain) was cleaved with PstI (75 U), and ligated to a PstI cassette in accordance with the method described in the manual of TaKaRa LA PCR in vitro Cloning Kit (supplied from TaKaRa). PCR was performed using the ligated mixture as the template, and a combination of a cassette primer C1 and a primer SEQA (SEQ ID NO:2) (94° C.: 30 seconds, 50° C.: 30 seconds, 72° C.: 4 minutes; 30 cycles). Then, the second PCR was performed using this PCR solution as the template and using a cassette primer C2 and a primer SEQB (SEQ ID NO:3) (94° C.: 30 seconds, 50° C.: 30 seconds, 72° C.: 4 minutes; 30 cycles). Amplification of a fragment having a length about 0.6 kb was confirmed, and the fragment was ligated to pT7Blue Teasy (Novagen). Escherichia coli JM109 was transformed with the plasmid containing the amplified fragment.

The nucleotide sequence of the approximately 0.6 kb fragment was determined, and it was found to include the nucleotide sequence encoding the N-terminal amino acid sequence of the enzyme. Chromosomal DNA treated with various restriction enzymes were analyzed by Southern blotting using this approximately 0.6 kb gene fragment as a probe, and an about 5 kb fragment treated with SacI was confirmed to have a positive signal. Then, the chromosomal DNA treated with SacI was run on an agarose gel electrophoresis to purify the about 5 kb fragment, which was then ligated to a SacI site of pUC18. Escherichia coli JM109 was transformed with this reaction solution to make a library. Colony hybridization was performed using the above probe, a positive colony was obtained, and a plasmid was extracted. The resulting plasmid was designated as pUCRHMT5K. The nucleotide sequence inserted in pUCRHMT5K was sequenced, and an ORF encoding 365 amino acid residues was present (SEQ ID NO:4).

Example 4

Expression of 2-Benzylserine Hydroxymethyltransferase Gene Derived from Rhodococcus sp. (AJ110611 Strain) in Escherichia coli (Preparation of the Expressing Bacterium JM109/pTrp4)

1.1 kb of the ORF region of the 2-benzylserine hydroxymethyltransferase gene was amplified by PCR with pUCRHMT5K as the template, and using primers S11F (SEQ ID NO:6) and S12R (SEQ ID NO:7). The amplified fragment was treated with NdeI/BamHI, and ligated to pTrp4 vector (Journal of Molecular Catalysis B: Enzymatic, 2005, 32, 205-211) which had been previously treated with NdeI/BamHI. Escherichia coli JM109 was transformed with the resulting vector to obtain a transformant having a plasmid (pTrp4RHMT) containing the objective gene fragment. This transformant was designated as JM109/pTrp4RHMT.

3 ml of an LB medium containing 100 mg/lampicillin was inoculated with one loopful of JM109/pTrp4RHMT cells which had been cultured overnight in an LB agar medium containing 100 mg/l ampicillin, and then was cultured at 37° C. for 16 hours. The resulting microbial cells were collected by centrifugation, and washed with 50 mM potassium phosphate buffer (pH 7.4) containing 0.1 mM pyridoxal phosphate. A microbial cell suspension was prepared using 0.3 mL of the same buffer. The microbial cell suspension was sonicated to disrupt the microbial cells. A supernatant obtained by centrifugation (18,000×g, 10 minutes, 4° C.) was used as a cell-free extract solution. The 2-benzylserine hydroxymethyltransferase activity in the resulting cell-free extract solution was measured, and was 0.017 U/mg. The activity in the cell-free extract solution obtained in the same manner as in the above method except using JM/pTrp4, the transformant obtained by transforming JM109 with pTrp4 in which no PCR product had been inserted was detection limit or less.

Example 5

Expression of 2-Benzylserine Hydroxymethyltransferase Gene Derived from Rhodococcus sp. (AJ110611 Strain) in Escherichia coli (Preparation of the Expressing Bacterium JM109/pSFNRHMT)

The plasmid pTrp4RHMT made in Example 4 was treated with BamHI, subsequently blunt-ended in accordance with the method described in the manual of TaKaRa DNA Blunting Kit (TaKaRa), and then treated with NdeI to prepare the 2-benzylserine hydroxymethyltransferase gene. Subsequently, pSFN vector (International Publication WO2006/075486 Pamphlet) was treated with PstI, then blunt-ended in accordance with the method described in the manual of TaKaRa DNA Blunting Kit (TaKaRa), and treated with NdeI. This vector was ligated to the gene previously prepared. Escherichia coli JM109 was transformed with this ligation product to obtain a transformant having a plasmid containing the objective gene fragment (pSFNRHMT). This transformant was designated as JM109/pSFNRHMT.

3 ml of the LB medium containing 100 mg/l ampicillin was inoculated with one loopful of JM109/pSFNRHMT which had been cultured overnight in the LB agar medium containing 100 mg/lampicillin, and then was cultured at 37° C. for 20 hours. The resulting microbial cells were collected by centrifugation, and washed with 50 mM potassium phosphate buffer (pH 7.4) containing 0.1 mM pyridoxal phosphate. A microbial cell suspension was prepared using 0.3 mL of the same buffer. The microbial cell suspension was sonicated to disrupt the microbial cells. A supernatant obtained by centrifugation (18,000×g, 10 minutes, 4° C.) was used as a cell-free extract solution. The 2-benzylserine hydroxymethyltransferase activity in the resulting cell-free extract solution was measured, and was 0.014 U/mg.

Example 6

Generation of α-benzyl-L-serine by 2-benzylserine hydroxymethyltransferase Derived from *Rhodococcus* sp. (AJ110611 Strain) via the BnS Synthesis Reaction by the Wild-Type Strain 50 µl of the purified enzyme solution prepared in Example 2 was added to a solution of 10 mM formaldehyde, 30 mM L-phenylalanine, 0.1 mM pyridoxal phosphate and 50 mM potassium phosphate buffer (pH 7.4), and the mixture was allowed to react at 30° C. for 30 minutes. A special grade formaldehyde solution [code number: 16223-55] supplied from Nacalai Tesque Inc. was used as formaldehyde. After completion of the reaction, 100 µl of 4 mM copper sulfate was added to 100 µl of the reaction mixture, which was then analyzed by HPLC using SumichiralOA-5000 (Sumika Chemical Analysis Service Ltd.) (Mobile phase: aqueous solution of 2 mM copper sulfate (10% isopropyl alcohol), column temperature: 30° C., flow rate: 1 ml/minute, detection: UV 230 nm). As a result, it was confirmed that 8.9 mM α-benzyl-L-serine had been formed.

Example 7

Stereological Determination of the Benzylserine Formed by the Enzymatic Reaction In order to synthesize α-benzyl-L-serine (Angew. Chem. Int. Ed. 2004, 43, 2382-2385), 1.41 ml of triethylamine was added to a methylene chloride solution in which 939.2 mg of ethyl benzimidate hydrochloride and 1 g of L-serine-tert-butyl ester hydrochloride had been dissolved. The mixture was heated and refluxed for 2.5 hours, and stirred at room temperature for 19 hours. 50 ml of methylene chloride was added to the reaction mixture, which was then washed twice with 20 mL of water, and dried on magnesium sulfate. Magnesium sulfate was removed, and then the solvent was evaporated. A residue was purified by silica gel chromatography (hexane/ethyl acetate, 5/1 to 4/1). After evaporating the solvent, 759 mg of 2-phenyl-2-oxazoline-4-carboxylate tert-butyl ester was yielded. 0.12 ml of benzyl bromide was added to a toluene solution in which 52.4 mg of 2-phenyl-2-oxazoline-4-carboxylate tert-butyl ester, 56.1 mg of potassium hydroxide and 9.55 mg of (S,S)-3,4,5-trifluorophenyl-NAS bromide (Wako Pure Chemical Industries Ltd., code number: 201-16401) had been suspended. The resulting mixture was stirred at 0° C. for 8 hours. 20 ml of ethyl acetate was added to the reaction mixture, which was then washed twice with 5 mL of water, and dried on magnesium sulfate. Magnesium sulfate was removed, and then the solvent was evaporated. A residue was purified by silica gel chromatography (hexane/ethyl acetate, 8/1 to 5/1). After evaporating the solvent, 51 mg of 4-benzyl 2-phenyl-2-oxazoline-4-carboxylate tert-butyl ester was obtained. This was analyzed by HPLC using CHIRALPAK OD-H (4.6×250 mm) (Mobile phase: hexane/isopropyl alcohol=99/1, column temperature: room temperature, flow rate: 1 ml/minute, detection: UV 210 nm), and its optical purity was 98.4% e.e. 1 ml of ethanol and 0.5 ml of a 6 N sodium hydroxide solution were added to 42 mg of 4-benzyl 2-phenyl-2-oxazoline-4-carboxylic acid tert-butyl ester, which was then heated and refluxed for 1 hour. Then 1 ml of 6 N HCl was added, and the reaction mixture was heated and refluxed for 2 hours. The reaction mixture was neutralized and impurities were removed to obtain a solution containing α-benzyl-L-serine.

The resulting solution containing α-benzyl-L-serine was analyzed by HPLC using SumichiralOA-5000 (Sumika Chemical Analysis Service Ltd.) (Mobile phase: aqueous solution of 2 mM copper sulfate (10% isopropyl alcohol), column temperature: 30° C., flow rate: 1 ml/minute, detection: UV 230 nm). As a result, it was found that this has the same retention time as α-benzylserine obtained from the enzymatic reaction. From the above results, it was found that as α-benzylserine obtained from the enzymatic reaction was α-benzyl-L-serine.

Example 8

Generation of α-benzyl-L-serine by *Escherichia coli* that Expresses 2-Benzylserine Hydroxymethyltransferase Gene Derived from *Rhodococcus* sp. (AJ110611 Strain) (BnS Synthesis by the Expressing Bacterium JM109/pTrp4RHMT: CFE)

3 ml of the LB medium containing 100 mg/l ampicillin was inoculated with one loopful of JM109/pTrp4RHMT cells which had been cultured overnight in the LB agar medium containing 100 mg/l ampicillin, and then was cultured at 37° C. for 16 hours. The resulting microbial cells were collected by centrifugation, and washed with 50 mM potassium phosphate buffer (pH 7.4) containing 0.1 mM pyridoxal phosphate. A microbial cell suspension was prepared using 0.3 ml of the same buffer. The microbial cell suspension was sonicated to disrupt the microbial cells. A supernatant obtained by centrifugation (18,000×g, 10 minutes, 4° C.) was used as a cell-free extract solution. 30 µl of the cell-free extract solution was added to a solution of 10 mM formaldehyde, 30 mM L-phenylalanine, 0.1 mM pyridoxal phosphate and 50 mM potassium phosphate buffer (pH 7.4), and the mixture was reacted at 30° C. for 30 minutes. A special grade formaldehyde solution [code number: 16223-55] supplied from Nacalai Tesque Inc. was used. After the completion of the reaction, 100 µl of 4 mM copper sulfate was added to 100 µl of the reaction mixture.

Then, 100 µl of water was added to 100 µl of the resulting solution, which was then analyzed by HPLC using SumichiralOA-5000 (Sumika Chemical Analysis Service Ltd.) (Mobile phase: aqueous solution of 2 mM copper sulfate (10% isopropyl alcohol), column temperature: 30° C., flow rate: 1 ml/minute, detection: UV 230 nm). As a result, it was confirmed that 5.2 mM α-benzyl-L-serine had been formed. The activity in the cell-free extract solution obtained in the same manner as in the above method except using JM109/pTrp4, the transformant obtained by transforming JM109 with pTrp4 in which no PCR product had been inserted was detection limit or less.

Example 9

Generation of α-benzyl-L-serine by *Escherichia coli* Expressing the 2-benzylserine Hydroxymethyltransferase Gene Derived from *Rhodococcus* sp. (AJ110611 Strain) (BnS Synthesis by the Expressing Bacterium JM109/pSFNRHMT: CFE)

3 ml of the LB medium containing 100 mg/l ampicillin was inoculated with one loopful of JM109/pSFNRHMT cells which had been cultured overnight in the LB agar medium containing 100 mg/l ampicillin, and then was cultured at 37° C. for 17 hours. The resulting microbial cells were collected by centrifugation, and washed with 50 mM potassium phosphate buffer (pH 7.4) containing 0.1 mM pyridoxal phosphate. A microbial cell suspension was prepared using 0.3 ml of the same buffer. The microbial cell suspension was sonicated to disrupt the microbial cells. A supernatant obtained by centrifugation (18,000×g, 10 minutes, 4° C.) was used as a cell-free extract solution. 30 µl of the cell-free extract solution was added to the solution of 10 mM formaldehyde, 30 mM L-phenylalanine, 0.1 mM pyridoxal phosphate and 50 mM potassium phosphate buffer (pH 7.4), and the mixture was allowed to react at 30° C. for one hour. A special grade formaldehyde solution [code number: 16223-55] supplied from Nacalai Tesque Inc. was used. After the completion of the reaction, 100 µl of 4 mM copper sulfate was added to 100 µl of the reaction mixture, which was then analyzed by HPLC using SumichiralOA-5000 (Sumika Chemical Analysis Service Ltd.) (Mobile phase: aqueous solution of 2 mM copper sulfate (10% isopropyl alcohol), column temperature: 30° C., flow rate: 1 ml/minute, detection: UV 230 nm). As a result, it was confirmed that 7.8 mM α-benzyl-L-serine had been formed.

Example 10

Generation of α-benzyl-L-serine by *Escherichia coli* Expressing the 2-benzylserine Hydroxymethyltransferase Gene Derived from *Rhodococcus* sp. (AJ110611 Strain) (BnS Synthesis by the Expressing Bacterium pSFNRHMT: Cell)

3 ml of the LB medium containing 100 mg/l ampicillin was inoculated with one loopful of JM109/pSFNRHMT cells which had been cultured overnight in the LB agar medium containing 100 mg/l ampicillin, and then was cultured at 37° C. for 16.5 hours. 50 ml of the LB medium containing 100 mg/l ampicillin in a 500 ml Sakaguchi flask was inoculated with 2.5 ml of the resulting microbial cell medium, and then cultured at 37° C. at 120 reciprocations/min for 17 hours. Microbial cells were collected from 10 ml of the resulting cultured medium by centrifugation (8,000×g, 10 minutes), and washed with 10 ml of 50 mM potassium phosphate buffer (pH 7.4) containing 0.1 mM pyridoxal phosphate. A microbial cell suspension was prepared using 10 mL of the same buffer. Then 100 µL of a solution of 10 mM formaldehyde, 30 mM L-phenylalanine, 0.1 mM pyridoxal phosphate and 50 mM potassium phosphate buffer (pH 7.4) was added to the microbial cells collected from 1 mL of the microbial cell suspension by centrifugation (18,000×g, 10 minutes). The mixture was reacted at 30° C. for 10 minutes. A special grade formaldehyde solution [code number: 16223-55] supplied from Nacalai Tesque Inc. was used. After the completion of the reaction, 100 µl of 4 mM copper sulfate was added to the reaction mixture, which was then centrifuged (18,000×g, 5 minutes) to separate the microbial cells. Then, the supernatant was analyzed by HPLC using SumichiralOA-5000 (Sumika Chemical Analysis Service Ltd.) (Mobile phase: aqueous solution of 2 mM copper sulfate (10% isopropyl alcohol), column temperature: 30° C., flow rate: 1 ml/minute, detection: UV 230 nm). As a result, it was confirmed that 6.2 mM α-benzyl-L-serine had been formed.

Example 11

Generation of α-isobutyl-serine by *Escherichia coli* that Expresses 2-benzylserine Hydroxymethyltransferase Gene Derived from *Rhodococcus* sp. (AJ110611 Strain) (iBuS Synthesis by the Expressing Bacterium pSFNRHMT: Cell)

50 ml of the LB medium containing 100 mg/l ampicillin in a 500 mL Sakaguchi flask was inoculated with one loopful of JM109/pSFNRHMT cells which had been cultured overnight in the LB agar medium containing 100 mg/l ampicillin, and was cultured with shaking at 37° C. at 120 reciprocations/min overnight. Microbial cells were collected from 10 mL of the resulting cultured medium by centrifugation (8,000×g, 10 minutes), and washed with 10 mL of 50 mM potassium phosphate buffer (pH 7.4) containing 0.1 mM pyridoxal phosphate. A microbial cell suspension was prepared using 10 ml of the same buffer. Then 100 µl of a solution composed of 10 mM formaldehyde, 30 mM L-leucine, 0.1 mM pyridoxal phosphate and 50 mM potassium phosphate buffer (pH 7.4) was added to the microbial cells collected from 1 ml of the microbial cell suspension by centrifugation (18,000×g, 10 minutes). The mixture was reacted at 30° C. for 30 minutes. A special grade formaldehyde solution [code number: 16223-55] supplied from Nacalai Tesque Inc. was used. After the completion of the reaction, 100 µl of 4 mM copper sulfate was added to the reaction mixture, which was then centrifuged (18,000×g, 5 minutes) to separate the microbial cells. Then, the supernatant was analyzed by HPLC using SumichiralOA-5000 (Sumika Chemical Analysis Service Ltd.) (Mobile phase: aqueous solution of 2 mM copper sulfate (5% isopropyl alcohol), column temperature: 30° C., flow rate: 1 ml/minute, detection: UV 230 nm). As a result, it was confirmed that 0.6 mM α-isobutyl-serine had been formed.

Reference Example

Synthesis of α-methylthioethyl-serine

In accordance with the literature (J. Peptide Sci., 2001, 7, 619-625), 10 g of DL-methionine was added to 20 ml of water and 11.5 ml of 6 N NaOH, and dissolved therein. While keeping pH at 10.5 to 11.5, 8.6 ml of benzoyl chloride was added thereto, and the mixture was stirred at room temperature for two hours. The resulting reaction mixture was filtrated and then washed with diethyl ether. Concentrated hydrochloric acid was gradually added to adjust the pH to 1 to precipitate a crystal. The crystal was filtrated, washed with water, and dried under reduced pressure to obtain 16.2 g of N-benzoylmethionine. 24 ml of acetic anhydride was added to 4.9 g of obtained N-benzoylmethionine, the solution was heated at 100° C. for 4 hours, then cooled to room temperature, and the solvent was evaporated. The steps of adding 24 ml of toluene to the residue and evaporating the solvent were repeated twice. The, the residue was dissolved in 2.5 ml of pyridine, 10 ml of 35% formaldehyde solution was added, and the solution was stirred at room temperature for 17 hours. 40 ml of water was added to the resulting reaction solution, which was then extracted with 40 ml of ethyl acetate. The extract was washed with water and saturated brine, and dried on magnesium sulfate. Magnesium sulfate was removed and the solvent was evaporated. The residue was purified by silica gel chromatography (hexane/ethyl acetate 4/1 to 1/1). After evaporating the solvent, 2.56 g of 5-benzoylamino-5-methylthioethyl-4-oxo-1,3-dioxane was obtained. 7.5 ml of 6 N hydrochloric acid was added to 1.06 g of the obtained 5-benzoylamino-5-methylthioethyl-4-oxo-1,3-dioxane, which was then heated and refluxed for 7 hours. The reaction solution was filtrated, and then the solvent was evaporated. 5 ml of water was added to the residue, which was then purified using an ion exchange resin (Amberlite 120). After evaporating the solvent, the resulting crystal was recrystallized from water/ethanol, and dried under reduced pressure to obtain 129 mg of α-methylthioethyl-serine. NMR of this compound was measured, and almost agreed with the values described in the literature.

Example 12

Synthesis of α-Methylthioethyl-Serine by *Escherichia coli* Expressing the 2-benzylserine hydroxymethyltransferase Gene Derived From *Rhodococcus* sp. (AJ110611 Strain) (HmMet Synthesis by the Expressing Bacterium pSFNRHMT: Cell)

50 ml of the LB medium containing 100 mg/l ampicillin in a 500 ml Sakaguchi flask was inoculated with one loopful of JM109/pSFNRHMT cells which had been cultured overnight in the LB agar medium containing 100 mg/l ampicillin, and then was cultured with shaking at 37° C. at 120 reciprocations/min overnight. Microbial cells were collected from 10 ml of the resulting cultured medium by centrifugation (8,000×g, 10 minutes), and washed with 10 ml of 50 mM potassium phosphate buffer (pH 7.4) containing 0.1 mM pyridoxal phosphate. A microbial cell suspension was prepared using 10 ml of the same buffer. Then 100 µl of a solution composed of 10 mM formaldehyde, 30 mM L-methionine, 0.1 mM pyridoxal phosphate and 50 mM potassium phosphate buffer (pH 7.4) was added to the microbial cells collected from 1 ml of the microbial Cell suspension by centrifugation (18,000×g, 10 minutes). The mixture was allowed to react at 30° C. for 30 minutes. A special grade formaldehyde solution [code number: 16223-55] supplied from Nacalai Tesque Inc. was used. After the completion of the reaction, 100 µl of 4 mM copper sulfate was added to the reaction mixture, which was then centrifuged (18,000×g, 5 minutes) to separate the microbial cells. Then, the supernatant was analyzed by HPLC using SumichiralOA-5000 (Sumika Chemical Analysis Service Ltd.) (Mobile phase: aqueous solution of 2 mM copper sulfate (2% isopropyl alcohol), column temperature: 30° C., flow rate: 1 ml/minute, detection: UV 230 nm). As a result, it was confirmed that 2.8 mM α-methylthioethyl-serine had been formed.

Example 13

Production of the Mutant Strains Y339S, Y339H, and Y339N pSFNRHMT made in Example 5 was used as the template in site-directed mutagenesis using PCR in order to construct mutant 2-benzylserine hydroxymethyltransferase. The mutation of Y339S was introduced using Quick change Site-Directed Mutagenesis Kit supplied from Stratagene (USA) in accordance with a protocol of its manufacturer and using the primer Y339SF (SEQ ID NO:8) and the primer Y339SR (SEQ ID NO:9), which both corresponded to the Y339S mutant enzyme. Likewise, the mutation of Y339H was introduced using the primer Y339HF (SEQ ID NO:10) and the primer Y339HR (SEQ ID NO:11), and the mutation of Y339N was introduced using the primer Y339NF (SEQ ID NO:12) and the primer Y339NR (SEQ ID NO:13). All of these primers correspond to the mutant enzymes, respectively. *Escherichia coli* JM109 was transformed with the PCR product, and transformants having a plasmid containing the objective gene fragment were obtained. These transformants were designated as JM109/pSFNRHMT-Y339S, JM109/pSFNRHMT-Y339H, and JM109/pSFNRHMT-Y339N, respectively.

Example 14

Reaction of the Mutant Strains Y339S, Y339H, and Y339N 3 ml of the LB medium containing 100 mg/l ampicillin was inoculated with JM109/pSFNRHMT-Y339S, JM109/pSFNRHMT-Y339H and JM109/pSFNRHMT-Y339N, respectively. The inoculated media were cultured at 37° C. overnight. The resulting microbial cells were collected by centrifugation (18,000×g, 10 minutes, 4° C.), and washed with 50 mM potassium phosphate buffer (pH 7.4) containing 0.1 mM pyridoxal phosphate. Microbial cell suspensions were prepared using 0.3 ml of the same buffer. The microbial cell suspensions were sonicated to disrupt the microbial cells. Supernatants obtained by centrifugation (18,000×g, 10 minutes, 4° C.) were used as cell-free extract solutions. 0.02 ml of the cell-free extract solution was added to a solution of 50 mM potassium phosphate buffer (pH 7.4), 10 mM α-benzyl-DL-serine, and 0.1 mM pyridoxal phosphate. The reaction mixture in a total amount of 0.06 ml was allowed to react at 30° C. for 10 minutes. After 10 minutes, the reaction was stopped by mixing 0.06 ml of the alkali reagent (5 N potassium hydroxide) attached in the formaldehyde kit, Test Wako (Wako Pure Chemicals Industries Ltd.). Subsequently, the detection reaction of formaldehyde was performed and the absorbance at 550 nm was measured in accordance with the manual attached to the kit. The amount of formaldehyde was obtained and the activity was calculated. Results are shown in Table 1.

TABLE 1

| Strain | U/mg |
| --- | --- |
| JM109/pSFNRHMT | 0.013 |
| JM109/pSFNRHMT-Y339S | 0.043 |
| JM109/pSFNRHMT-Y339H | 0.033 |
| JM109/pSFNRHMT-Y339N | 0.036 |

Example 15

Production of the Mutant Strain Y339S—N19S pSFNRHMT-Y339S made in Example 13 was used as the template in the site-directed mutagenesis using PCR in order to construct mutant 2-benzylserine hydroxymethyltransferase. The mutation was introduced using. Quick change Site-Directed Mutagenesis Kit supplied from Stratagene (USA) in accordance with the protocol of the manufacturer and using the primers N19SF (SEQ ID NO:14) and N19SR (SEQ ID NO:15), which both correspond to the mutant enzyme. *Escherichia coli* JM109 was transformed with a PCR product, and a transformant having a plasmid containing the objective gene fragment was obtained. This transformant was designated as JM109/pSFNRHMT-Y339S-N19S. 3 ml of the LB medium containing 100 mg/l ampicillin was inoculated with the prepared JM109/pSFNRHMT-Y339S-N19S. The inoculated medium was cultured at 37° C. overnight. The resulting microbial cells were collected by centrifugation (18,000×g, 10 minutes, 4° C.), and washed with 50 mM potassium phosphate buffer (pH 7.4) containing 0.1 mM pyridoxal phosphate. A microbial cell suspension was prepared using 0.3 ml of the same buffer. The microbial cell suspension was sonicated to disrupt the microbial cells. A supernatant obtained by centrifugation (18,000×g, 10 minutes, 4° C.) was used as a cell-free extract solution. 0.005 ml of the cell-free extract solution was added to a solution of 50 mM potassium phosphate buffer (pH 7.4), 10 mM α-benzyl-DL-serine and 0.1 mM pyridoxal phosphate. The reaction mixture in a total amount of 0.06 ml was allowed to react at 30° C. for 5 minutes. After 5 minutes, the reaction was stopped by mixing 0.06 ml of the alkali reagent (5 N potassium hydroxide) attached in the formaldehyde kit, Test Wako (Wako Pure Chemicals Industries Ltd.). Subsequently, the detection reaction of formaldehyde was performed and the absorbance at 550 nm was measured in accordance with the manual attached to the kit. The amount of the formaldehyde was obtained and the activity was calculated. The results are shown in Table 2.

TABLE 2

| Strain | U/mg |
|---|---|
| JM109/pSFNRHMT | 0.03 |
| JM109/pSFNRHMT-Y339S | 0.34 |
| JM109/pSFNRHMT-Y339S-N19S | 0.17 |

Example 16

Synthesis of BnS Using JM109/pSFNRHMT-Y339S 3 ml of the LB medium containing 100 mg/l ampicillin was inoculated with one loopful of JM109/pSFNRHMT-Y339S cells which had been cultured overnight in the LB agar medium containing 100 mg/l ampicillin, and cultured at 37° C. for 16.5 hours. 50 ml of the LB medium containing 100 mg/l ampicillin in a 500 ml Sakaguchi flask was inoculated with 2.5 ml of the resulting microbial cell medium, and cultured at 37° C. at 120 reciprocations/min for 17 hours. The microbial cells were collected from 10 ml of the resulting cultured medium by centrifugation (8,000×g, 10 minutes), and washed with 10 ml of 50 mM potassium phosphate buffer (pH 7.4) containing 0.1 mM pyridoxal phosphate. A microbial cell suspension was prepared using 10 ml of the same buffer. Then 100 μl of the solution of 10 mM formaldehyde, 30 mM L-phenylalanine, 0.1 mM pyridoxal phosphate, and 50 mM potassium phosphate buffer (pH 7.4) was added to the microbial cells collected from 0.2 ml of the microbial cell suspension by centrifugation (18,000×g, 10 minutes). The mixture was reacted at 30° C. for 10 minutes. A special grade formaldehyde solution [code number: 16223-55] supplied from Nacalai Tesque Inc. was used. After the completion of the reaction, 100 μl of 4 mM copper sulfate was added to the reaction mixture, which was then centrifuged (18,000×g, 5 minutes) to separate the microbial cells. Then, the supernatant was analyzed by HPLC using SumichiralOA-5000 (Sumika Chemical Analysis Service Ltd.) (Mobile phase: aqueous solution of 2 mM copper sulfate (10% isopropyl alcohol), column temperature: 30° C., flow rate: 1 ml/minute, detection: UV 230 nm). As a result, it was confirmed that α-benzyl-L-serine had been quantitatively formed.

Example 17

Synthesis of iBus Using JM109/pSFNRHMT-Y339S 50 ml of the LB medium containing 100 mg/l ampicillin in a 500 ml Sakaguchi flask was inoculated with one loopful of JM109/pSFNRHMT-Y339S cells which had been cultured overnight in the LB agar medium containing 100 mg/l ampicillin, and cultured with shaking at 37° C. at 120 reciprocations/min overnight. The microbial cells were collected from 10 ml of the resulting cultured medium by centrifugation (8,000×g, 10 minutes), and washed with 10 ml of 50 mM potassium phosphate buffer (pH 7.4) containing 0.1 mM pyridoxal phosphate. A microbial cell suspension was prepared using 10 ml of the same buffer. Then 100 μl of the solution composed of 10 mM formaldehyde, 30 mM L-leucine, 0.1 mM pyridoxal phosphate and 50 mM potassium phosphate buffer (pH 7.4) was added to the microbial cells collected from 1 ml of the microbial cell suspension by centrifugation (18,000×g, 10 minutes). The mixture was allowed to react at 30° C. for 30 minutes. A special grade formaldehyde solution [code number: 16223-55] supplied from Nacalai Tesque Inc. was used. After the completion of the reaction, 100 μl of 4 mM copper sulfate was added to the reaction mixture, which was then centrifuged (18,000×g, 5 minutes) to separate the microbial cells. Then, the supernatant was analyzed by HPLC using SumichiralOA-5000 (Sumika Chemical Analysis Service Ltd.) (Mobile phase: aqueous solution of 2 mM copper sulfate (5% isopropyl alcohol), column temperature: 30° C., flow rate: 1 ml/minute, detection: UV 230 nm). As a result, it was confirmed that 4.6 mM α-isobutyl-serine had been formed.

Example 18

Synthesis of BnS Using JM109/pSFNRHMT-Y339-N19S 350 ml of TB medium (12 g/l of trypton, 24 g/l of yeast extract, 2.3 g/l of potassium dihydrogen phosphate, 12.5 g/l of dipotassium hydrogen phosphate, 4 g/l of glycerol) containing 100 mg/l of ampicillin was inoculated with JM109/pSFNRHMT-Y339S-N19S cells which had been cultured overnight in the LB agar medium containing 100 mg/l ampicillin, and cultured at 37° C. for 17 hours. The microbial cells were collected by centrifugation (8,000×g, 10 minutes), washed with 50 ml of 50 mM potassium phosphate buffer (pH 7.4) containing 0.1 mM pyridoxal phosphate, and added to the reaction solution (30 mM L-phenylalanine, 45 mM formaldehyde, 0.1 mM pyridoxal phosphate and 50 mM potassium phosphate buffer (pH 7.4), 200 ml). The reaction mixture was stirred at 30° C. for 5 hours, and then, 100 μl of 4 mM copper sulfate and 80 μl of water were added to 20 μl of the reaction mixture, which was then centrifuged (18,000×g, 5 minutes) to separate the microbial cells. Then, the supernatant was analyzed by HPLC using SumichiralOA-5000 (Sumika Chemical Analysis Service Ltd.) (Mobile phase: aqueous solution of 2 mM copper sulfate (10% isopropyl alcohol), column temperature: 30° C., flow rate: 1 ml/minute, detection: UV 230 nm). As a result, it was confirmed that 28.2 mM α-benzyl-L-serine had been formed.

Example 19

Synthesis of BnS Using JM109/pSFNRHMT-Y339-N19S 700 ml of TB medium (12 g/l of trypton, 24 g/l of yeast extract, 2.3 g/l of potassium dihydrogen phosphate, 12.5 g/l of dipotassium hydrogen phosphate, 4 WI of glycerol) was inoculated with JM109/pSFNRHMT-Y339S-N19S cells which had been cultured overnight in the LB agar medium containing 100 mg/l ampicillin, and cultured at 37° C. for 17 hours. The cultured medium was divided into two (350 ml). The microbial cells were collected from each of them by centrifugation (8,000×g, 10 minutes), and washed with 50 ml of 50 mM potassium phosphate buffer (pH 7.4) containing 0.1 mM pyridoxal phosphate. The microbial cells corresponding to 350 ml of the culture medium were added to the reaction solution (60 mM L-phenylalanine, 90 mM formaldehyde, 0.1 mM pyridoxal phosphate and 50 mM potassium phosphate buffer (pH 7.4), 200 ml), which was then stirred at 30° C. for 6.5 hours. Then, the microbial cells corresponding to another 350 ml of the culture medium were added thereto, which was further stirred for 15 hours. After the completion of the reaction, 100 µl of 4 mM copper sulfate and 80 µl of water were added to 20 µl of the reaction mixture, which was then centrifuged (18,000×g, 5 minutes) to separate the microbial cells. Then, the supernatant was analyzed by HPLC using SumichiralOA-5000 (Sumika Chemical Analysis Service Ltd.) (Mobile phase: aqueous solution of 2 mM copper sulfate (10% isopropyl alcohol), column temperature: 30° C., flow rate: 1 ml/minute, detection: UV 230 nm). As a result, it was confirmed that 57.6 mM α-benzyl-L-serine had been formed.

Example 20

Purification of α-benzyl-L-serine

The microbial cells were removed from the reaction mixture obtained in Example 18 by centrifugation (8,000×g, 10 minutes). Sulfuric acid was added to the resulting solution to adjust the pH to 3, and the dissolved proteins were heated and agglutinated at 50° C. for 2 hours. This was filtrated with 0.2 µm MF. This solution was fed to a column filled with 40 ml of a strongly acidic cation exchange resin (Amberlite IR120 supplied from Aldrich) to adsorb α-benzyl-L-serine. Water in the amount of 2.5 times the amount of resin was run through the column to wash the resin, then the peptide was eluted using 1 M ammonia water and an eluant was collected every 10 ml. The obtained second to tenth fractions were concentrated under reduced pressure to almost remove ammonia. The obtained crystal was dried at 50° C. under reduced pressure overnight to yield 1.57 g (93 wt %) of α-benzyl-L-serine as the crystal.

Example 21

Purification of α-benzyl-L-serine 841 mg (22 wt %) of a crude crystal containing 184 mg of α-benzyl-L-serine, which had been obtained by the purification using the strongly acidic cation exchange resin (Amberlite IR120 supplied from Aldrich) like in Example 20 was dissolved in about 5 ml of water. This solution was fed to the column filled with 17 ml of a synthetic adsorbent (SP207 supplied from Mitsubishi Chemical Corporation), and eluted with the water. Fractions containing α-benzyl-L-serine were collected, concentrated under reduced pressure, and dried at 50° C. under reduced pressure overnight to yield 174 mg (97 wt %) of α-benzyl-L-serine as the crystal. An optical rotation of this crystal was measured, and was $[\alpha]^{20}_D$=+16.8 (C 0.79, $H_2O$), which agreed with the value described in the literature. Value in the literature. $[\alpha]^{20}_D$=+16.4 (C 0.81, $H_2O$) (Synlett 1997, 253.).

Example 22

Synthesis of α-methylthioethyl-L-serine 750 ml of the TB medium (12 g/l of trypton, 24 of yeast extract, 2.3 g/l of potassium dihydrogen phosphate, 12.5 g/l of dipotassium hydrogen phosphate, and 4 g/l of glycerol) containing 100 mg/l of ampicillin was inoculated with JM109/pSFNRHMT-Y339S-N19S cells which had been cultured overnight in the LB agar medium containing 100 mg/l of ampicillin, and cultured at 37° C. for 17 hours. The microbial cells were collected by centrifugation (8,000×g, 10 minutes), washed with 50 ml of 50 mM potassium phosphate buffer (pH 7.4) containing 0.1 mM pyridoxal phosphate, and added to a reaction solution (60 mM L-methionine, 90 mM formaldehyde, 0.1 mM pyridoxal phosphate and 50 mM potassium phosphate buffer (pH 7.4), 200 ml). The reaction mixture was stirred at 30° C. for 23 hours, and then 100 µl of 4 mM copper sulfate and 80 µl of water were added to 20 µl of the reaction mixture, which was then centrifuged (18,000×g, 5 minutes) to separate the microbial cells. Then, the supernatant was analyzed by HPLC using SumichiralOA-5000 (Sumika Chemical Analysis Service Ltd.) (Mobile phase: aqueous solution of 2 mM copper sulfate (2% isopropyl alcohol), column temperature: 30° C., flow rate: 1 ml/minute, detection: UV 230 nm). As a result, it was confirmed that 46 mM α-methylthioethyl-L-serine had been formed.

Example 23

Purification of α-methylthioethyl-L-serine 750 ml of the TB medium (12 g/l of trypton, 24 g/l of yeast extract, 2.3 g/l of potassium dihydrogen phosphate, 12.5 g/l of dipotassium hydrogen phosphate, and 4 g/l of glycerol) containing 100 mg/l of ampicillin was inoculated with JM109/pSFNRHMT-Y339S-N19S cells which had been cultured overnight in LB agar medium containing 100 mg/l ampicillin, and cultured at 37° C. for 17 hours. The cultured medium was divided into two (350 ml+400 ml). The microbial cells were collected from each of them by centrifugation (8,000×g, 10 minutes), and washed with 50 ml of 50 mM potassium phosphate buffer (pH 7.4) containing 0.1 mM pyridoxal phosphate. The microbial cells corresponding to 350 ml of the culture medium were added to the reaction solution (60 mM L-methionine, 90 mM formaldehyde, 0.1 mM pyridoxal phosphate and 50 mM potassium phosphate buffer (pH 7.4), 200 ml), which was then stirred at 30° C. for 4 hours. The microbial cells corresponding to 400 ml of the cultured medium were added and the mixture was stirred for additional 18 hours. The microbial cells and formaldehyde were added depending on residual amounts. The microbial cells were simply removed from the reaction mixture by centrifugation (8,000×g, 10 minutes). Sulfuric acid was added to the resulting solution to adjust pH to 2.5, and dissolved proteins were heated and agglutinated at 50° C. for one hour. Insoluble matter were removed by centrifugation (8,000×g, 10 minutes). The solution was filtrated with 0.45 μm MF. This solution was fed to the column filled with 40 ml of the strongly acidic cation exchange resin (Amberlite IR120 supplied from Aldrich) to adsorb α-methylthioethyl-L-serine. Water in an amount of 2.5 times the amount of resin was run through the column to wash the resin, then the peptide was eluted using 1 M ammonia water and an eluant was collected every 10 ml. The obtained second to tenth fractions were concentrated under reduced pressure to almost remove ammonia. The obtained crystal was dried at 50° C. under reduced pressure overnight to yield 1.40 g (98 wt %) of α-methylthioethyl-L-serine as the crystal. The optical rotation of this crystal was measured, and was $[\alpha]^{20}_D=-21.7$ (C 1, 5N HCl), which agreed with the value described in the literature. Value in the literature $[\alpha]^{20}_D=-10.5$ (C 1, 5N HCl)(J. Peptide Sci., 2001, 7, 619.)

Example 24

Synthesis of α-methylserine 50 ml of the LB medium containing 100 mg/l ampicillin in a 500 ml Sakaguchi flask was inoculated with JM109/pSFN-RHMT-Y339S cells which had been cultured overnight in LB agar medium containing 100 mg/l ampicillin, and cultured at 37° C. at 120 reciprocations/min for 17 hours. Microbial cells were collected by centrifugation (8,000×g, 10 minutes), and washed with 30 ml of 50 mM potassium phosphate buffer (pH 7.4) containing 0.1 mM pyridoxal phosphate. A microbial cell suspension was prepared using 50 ml of the same buffer. Then 100 μl of a solution of 10 mM formaldehyde, 30 mM L-alanine, 0.1 mM pyridoxal phosphate and 50 mM potassium phosphate buffer (pH 7.4) was added to the microbial cells collected from 2 ml of the microbial cell suspension by centrifugation (18,000×g, 10 minutes). The mixture was allowed to react at 30° C. for one hour. After the completion of the reaction, an ESI-MS analysis was performed using a supernatant obtained by centrifugation (18,000×g, 5 minutes, 4° C.), and a molecular ion peak of α-methylserine was observed.

Example 25

Synthesis of α-carbamoylmethylserine 50 ml of the LB medium containing 100 mg/l ampicillin in a 500 ml Sakaguchi flask was inoculated with JM109/pSFN-RHMT-Y339S cells which had been cultured overnight in the LB agar medium containing 100 mg/l ampicillin, and cultured at 37° C. at 120 reciprocations/min for 17 hours. Microbial cells were collected by centrifugation (8,000×g, 10 minutes), and washed with 30 ml of 50 mM potassium phosphate buffer (pH 7.4) containing 0.1 mM pyridoxal phosphate. A microbial cell suspension was prepared using 50 ml of the same buffer. Then 100 ml of a solution composed of 10 mM formaldehyde, 30 mM L-asparagine, 0.1 mM pyridoxal phosphate and 50 mM potassium phosphate buffer (pH 7.4) was added to the microbial cells collected from 2 ml of the microbial cell suspension by centrifugation (18,000×g, 10 minutes). The mixture was reacted at 30° C. for one hour. After the completion of the reaction, the ESI-MS analysis was performed using a supernatant obtained by centrifugation (18,000×g, 5 minutes, 4° C.), and a molecular ion peak of α-carbamoylmethylserine was observed.

Example 26

Synthesis of α-thiomethylserine 50 ml of the LB medium containing 100 mg/l ampicillin in a 500 ml Sakaguchi flask was inoculated with JM109/pSFN-RHMT-Y339S cells which had been cultured overnight in the LB agar medium containing 100 mg/l ampicillin, and cultured at 37° C. at 120 reciprocations/min for 17 hours. Microbial cells were collected by centrifugation (8,000×g, 10 minutes), and washed with 30 ml of 50 mM potassium phosphate buffer (pH 7.4) containing 0.1 mM pyridoxal phosphate. A microbial cell suspension was prepared using 50 ml of the same buffer. Then 100 μl of a solution of 10 mM formaldehyde, 30 mM L-cysteine, 0.1 mM pyridoxal phosphate and 50 mM potassium phosphate buffer (pH 7.4) was added to the microbial cells collected from 2 ml of the microbial cell suspension by centrifugation (18,000×g, 10 minutes). The mixture was reacted at 30° C. for one hour. After the completion of the reaction, ESI-MS analysis was performed using a supernatant obtained by centrifugation (18,000×g, 5 minutes, 4° C.), and a molecular ion peak of α-thiomethylserine was observed.

Example 27

Synthesis of α-indolemethylserine 50 ml of the LB medium containing 100 mg/l ampicillin in a 500 ml Sakaguchi flask was inoculated with JM109/pSFN-RHMT-Y339S cells which had been cultured overnight in the LB agar medium containing 100 mg/l ampicillin, and cultured at 37° C. at 120 reciprocations/min for 17 hours. Microbial cells were collected by centrifugation (8,000×g, 10 minutes), and washed with 30 ml of 50 mM potassium phosphate buffer (pH 7.4) containing 0.1 mM pyridoxal phosphate. A microbial cell suspension was prepared using 50 ml of the same buffer. Then 100 μl of a solution of 10 mM formaldehyde, 30 mM L-tryptophan, 0.1 mM pyridoxal phosphate and 50 mM potassium phosphate buffer (pH 7.4) was added to the microbial cells collected from 2 ml of the microbial cell suspension by centrifugation (18,000×g, 10 minutes). The mixture was reacted at 30° C. for one hour. After the completion of the reaction, ESI-MS analysis was performed using a supernatant obtained by centrifugation (18,000×g, 5 minutes, 4° C.), and a molecular ion peak of α-indolemethylserine was observed.

Example 28

Synthesis of α-sec-butylserine 50 ml of the LB medium containing 100 mg/l ampicillin in a 500 ml Sakaguchi flask was inoculated with JM109/pSFN-RHMT-Y339S cells which had been cultured overnight in the LB agar medium containing 100 mg/l ampicillin, and cultured at 37° C. at 120 reciprocations/min for 17 hours. Microbial cells were collected by centrifugation (8,000×g, 10 minutes), and washed with 30 ml of 50 mM potassium phosphate buffer (pH 7.4) containing 0.1 mM pyridoxal phosphate. A microbial cell suspension was prepared using 50 ml of the same buffer. Then 100 μl of a solution of 10 mM formaldehyde, 30 mM L-isoleucine, 0.1 mM pyridoxal phosphate and 50 mM potassium phosphate buffer (pH 7.4) was added to the microbial cells collected from 2 ml of the microbial cell suspension by centrifugation (18,000×g, 10 minutes). The mixture was reacted at 30° C. for one hour. After the completion of the reaction, ESI-MS analysis was performed using a supernatant obtained by centrifugation (18,000×g, 5 minutes, 4° C.), and a molecular ion peak of α-sec-butylserine was observed.

Example 29

Synthesis of α-p-hydroxy-benzylserine 50 ml of TB medium (12 g/l of trypton, 24 g/l of yeast extract, 2.3 g/l of potassium dihydrogen phosphate, 12.5 g/l of dipotassium hydrogen phosphate, and 4 g/l of glycerol) containing 100 mg/l of ampicillin was inoculated with JM109/pSENRHMT-Y339S-N19S cells which had been cultured overnight in LB agar medium containing 100 mg/l ampicillin, and cultured at 37° C. for 18 hours. The microbial cells were collected by centrifugation, washed with 50 ml of 50 mM potassium phosphate buffer (pH 7.4) containing 0.1 mM pyridoxal phosphate. A microbial cell suspension was prepared using 5 ml of the same buffer. The microbial cell suspension was sonicated to disrupt the microbial cells. A supernatant obtained by centrifugation (18,000×g, 10 minutes, 4° C.) was used as a cell-free extract solution. 53.3 μl of the obtained cell-free extract solution was added to a solution of 1 mM L-tyrosine, 3 mM formaldehyde, 0.1 mM pyridoxal phosphate and 50 mM potassium phosphate buffer (pH 7.4). The mixture was reacted at 30° C. for one hour. After the completion of the reaction, ESI-MS analysis was performed using a supernatant obtained by centrifugation (18,000×g, 5 minutes, 4° C.), and a molecular ion peak of α-p-hydroxy-benzylserine was observed.

Example 30

Synthesis of α-cyclohexylmethylserine 50 ml of the LB medium containing 100 mg/l ampicillin was inoculated with JM109/pSFNRHMT-Y339S—N19S cells which had been cultured overnight in the LB agar medium containing 100 mg/l ampicillin, and cultured at 37° C. for 17 hours. The microbial cells were collected by centrifugation, and washed with 50 ml of 50 mM potassium phosphate buffer (pH 7.4) containing 0.1 mM pyridoxal phosphate. A microbial cell suspension was prepared using 5 ml of the same buffer. The microbial cell suspension was sonicated to disrupt the microbial cells. A supernatant obtained by centrifugation (18,000×g, 10 minutes, 4° C.) was used as a cell-free extract solution. 59 μl of the obtained cell-free extract solution was added to a solution of 12.5 mM cyclohexylalanine, 3 mM formaldehyde, 0.1 mM pyridoxal phosphate and 50 mM potassium phosphate buffer (pH 7.4). The mixture was reacted at 30° C. for 30 minutes. After the completion of the reaction, ESI-MS analysis was performed using a supernatant obtained by centrifugation (18,000×g, 5 minutes, 4° C.), and a molecular ion peak of α-cyclohexylmethylserine was observed.

Example 31

Synthesis of Methylserine Using JM109/pSFNRHMT-Y339S—N19S 50 ml of TB medium (12 g/l of trypton, 24 g/l of yeast extract, 2.3 g/l of potassium dihydrogen phosphate, 12.5 g/l of dipotassium hydrogen phosphate, and 4 g/l of glycerol) containing 100 mg/l of ampicillin in a 500 ml Sakaguchi flask was inoculated with JM109/pSFNRHMT-Y339S-N19S cells which had been cultured overnight in the LB agar medium containing 100 mg/l of ampicillin, and cultured at 37° C. at 120 reciprocations/min for 16 hours. The microbial cells were collected from 10 ml of the cultured medium by centrifugation (8,000×g, 10 minutes), and then washed with 10 ml of 50 mM potassium phosphate buffer (pH 7.4) containing 0.1 mM pyridoxal phosphate. A microbial cell suspension was prepared using 10 ml of the same buffer. Then 100 μl of the solution composed of 30 mM formaldehyde, 30 mM L-alanine, 0.1 mM pyridoxal phosphate and 50 mM potassium phosphate buffer (pH 7.4) was added to the microbial cells collected from 1 ml of the microbial cell suspension by centrifugation (18,000×g, 10 minutes). The mixture was allowed to react at 30° C. for one hour. A special grade formaldehyde solution [code number: 16223-55] supplied from Nacalai Tesque Inc. was used. After the completion of the reaction, 100 μl of 4 mM copper sulfate was added to the reaction mixture, which was then centrifuged (18,000×g, 5 minutes) to separate the microbial cells. 100 μl of water was added to 100 μl of the resulting solution, which was then analyzed by HPLC using SumichiralOA-5000 (Sumika Chemical Analysis Service Ltd.) (Mobile phase: aqueous solution of 0.5 mM copper sulfate, column temperature: 30° C., flow rate: 1 ml/minute, detection: UV 230 nm). As a result, it was confirmed that 3.4 mM α-methyl-L-serine had been formed.

Example 32

Synthesis of α-ethylserine 50 ml of the LB medium containing 100 mg/l of ampicillin in a 500 ml Sakaguchi flask was inoculated with JM109/pSFNRHMT-Y339S cells which had been cultured overnight in the LB agar medium containing 100 mg/l ampicillin, and cultured at 37° C. at 120 reciprocations/min for 17 hours. The microbial cells were collected from 10 ml of the cultured medium by centrifugation (8,000×g, 10 minutes), and then washed with 10 ml of 50 mM potassium phosphate buffer (pH 7.4) containing 0.1 mM pyridoxal phosphate. A microbial cell suspension was prepared using 10 ml of the same buffer. Then 100 μl of a solution of 10 mM formaldehyde, 30 mM S-2-amino-n-butyric acid, 0.1 mM pyridoxal phosphate and 50 mM potassium phosphate buffer (pH 7.4) was added to the microbial cells collected from 2 ml of the microbial cell suspension by centrifugation (18,000×g, 5 minutes, 4° C.). The mixture was allowed to react at 30° C. for one hour. After the completion of the reaction, ESI-MS analysis was performed using a supernatant obtained by centrifugation (18,000×g, 5 minutes, 4° C.), and a molecular ion peak of α-ethylserine was observed.

Example 33

Synthesis of α-propylserine 50 ml of the LB medium containing 100 mg/l of ampicillin in a 500 ml Sakaguchi flask was inoculated with JM109/pSFNRHMT-Y339S cells which had been cultured overnight in the LB agar medium containing 100 mg/l ampicillin, and cultured at 37° C. at 120 reciprocations/min for 17 hours. The microbial cells were collected from 10 ml of the cultured medium by centrifugation (8,000×g, 10 minutes), and then washed with 10 ml of 50 mM potassium phosphate buffer (pH 7.4) containing 0.1 mM pyridoxal phosphate. A microbial cell suspension was prepared using 10 ml of the same buffer. Then 100 μl of a solution composed of 10 mM formaldehyde, 30 mM L-norvaline, 0.1 mM pyridoxal phosphate and 50 mM potassium phosphate buffer (pH 7.4) was added to the microbial cells collected from 2 ml of the microbial cell suspension by centrifugation (18,000×g, 5 minutes, 4° C.). The mixture was allowed to react at 30° C. for one hour. After the completion of the reaction, ESI-MS analysis was performed using a supernatant obtained by centrifugation (18,000×g, 5 minutes, 4° C.), and a molecular ion peak of α-propylserine was observed.

Example 34

Synthesis of α-butylserine 50 ml of the LB medium containing 100 mg/l of ampicillin in a 500 ml Sakaguchi flask was inoculated with JM109/pSFNRHMT-Y339S cells which had been cultured overnight in the LB agar medium containing 100 mg/l ampicillin, and cultured at 37° C. at 120 reciprocations/min for 17 hours. The microbial cells were collected from 10 ml of the cultured medium by centrifugation (8,000×g, 10 minutes), and then washed with 10 ml of 50 mM potassium phosphate buffer (pH 7.4) containing 0.1 mM pyridoxal phosphate. A microbial cell suspension was prepared using 10 ml of the same buffer. Then 100 μl of a solution of 10 mM formaldehyde, 30 mM L-norleucine, 0.1 mM pyridoxal phosphate and 50 mM potassium phosphate buffer (pH 7.4) was added to the microbial cells collected from 2 ml of the microbial cell suspension by centrifugation (18,000×g, 5 minutes, 4° C.). The mixture was allowed to react at 30° C. for one hour. After the completion of the reaction, the ESI-MS analysis was performed using a supernatant obtained by centrifugation (18,000×g, 5 minutes, 4° C.), and a molecular ion peak of α-butylserine was observed.

Example 35

Synthesis of Methylserine Using Cell-Free Extract Solution of JM109/pSFNRHMT-Y339S-N19S 50 ml of TB medium (12 g/l of trypton, 24 g/l of yeast extract, 2.3 g/l of potassium dihydrogen phosphate, 12.5 g/l of dipotassium hydrogen phosphate, and 4 g/l of glycerol) containing 100 mg/l of ampicillin in a 500 ml Sakaguchi flask was inoculated with JM109/pSFNRHMT-Y339S-N19S cells which had been cultured overnight in LB agar medium containing 100 mg/l of ampicillin, and cultured at 37° C. at 120 reciprocations/min for 16 hours. The microbial cells were collected from 40 ml of the cultured medium by centrifugation (8,000×g, 10 minutes), and then washed with 40 ml of 50 mM potassium phosphate buffer (pH 7.4) containing 0.1 mM pyridoxal phosphate. A microbial cell suspension was prepared using 4 ml of the same buffer. The microbial cell suspension was sonicated to disrupt the microbial cells. A supernatant obtained by centrifugation (18,000×g, 5 minutes, 4° C.) was used as a cell-free extract solution. 0.034 ml of the resulting cell-free extract solution was added to the reaction solution of 30 mM formaldehyde, 30 mM L-alanine, 0.1 mM pyridoxal phosphate and 50 mM potassium phosphate buffer (pH 7.4) to make a reaction mixture in a total amount of 0.1 ml. The reaction mixture was allowed to react at 30° C. for one hour. A special grade formaldehyde solution [code number: 16223-55] supplied from Nacalai Tesque Inc. was used. After the completion of the reaction, 100 μl of 4 mM copper sulfate was added to the reaction mixture, and centrifuged (18,000×g, 5 minutes, 4° C.). Then, 100 μl of water was added to 100 μl of the resulting solution, which was then analyzed by HPLC using SumichiralOA-5000 (Sumika Chemical Analysis Service Ltd.) (Mobile phase: aqueous solution of 0.5 mM copper sulfate, column temperature: 30° C., flow rate: 1 ml/minute, detection: UV 230 nm). As a result, it was confirmed that 19.5 mM α-methyl-L-serine had been formed.

Industrial Applicability

The present invention is useful in industries involved in the production of amino acids.

The present invention is expected to contribute to the production of the various serine derivatives and the optically active amino acids and to be used, for example, for producing pharmaceutical intermediates.

Sequence Listing

SEQ ID NO:1 N-terminal amino acid sequence of 2-benzylserine hydroxymethyltransferase derived from *Rhodococcus* sp. (AJ110611 strain)
SEQ ID NO:2 Primer SEQA
SEQ ID NO:3 Primer SEQB
SEQ ID NO:4 Nucleic acid sequence (ORF) encoding 2-benzylserine hydroxymethyltransferase derived from *Rhodococcus* sp. (AJ110611 strain)
SEQ ID NO:5 Amino acid sequence of 2-benzylserine hydroxymethyltransferase derived from *Rhodococcus* sp. (AJ110611 strain)
SEQ ID NO:6 Primer S11F
SEQ ID NO:7 Primer S12R
SEQ ID NO:8 Primer Y339SF
SEQ ID NO:9 Primer Y339SR
SEQ ID NO:10 Primer Y339HF
SEQ ID NO:11 Primer Y339HR
SEQ ID NO:12 Primer Y339NF
SEQ ID NO:13 Primer Y339NR
SEQ ID NO:14 Primer N19SF
SEQ ID NO:15 Primer N19SR

The invention claimed is:

1. An isolated polynucleotide encoding a protein selected from the group consisting of:
   (A) a protein comprising the amino acid sequence of SEQ ID NO:5, and
   (B) a protein comprising the amino acid sequence of SEQ ID NO:5, but which includes substitution, deletion, insertion and/or addition of one to 20 amino acids, and wherein said protein is able to catalyze a reaction in which an α-amino acid of formula (1):

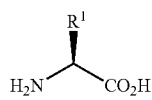   (I)

is reacted with an aldehyde of formula (II):

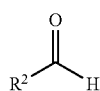   (II)

to form a serine derivative of formula (III):

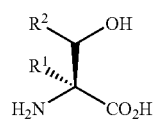   (III)

wherein R¹ is selected from the group consisting of an alkyl group having 1 to 7 carbon atoms, an aryl group having 6 to 14 carbon atoms, a cycloalkyl group having 3 to 10 carbon atoms, an aralkyl group having 7 to 19 carbon atoms, an alkoxyalkyl group having 2 to 11 carbon atoms, a group containing a hetero atom in the carbon skeleton thereof, and a group containing a carbon-carbon unsaturated bond in the carbon skeleton thereof, wherein these groups may be straight or branched, may have alicyclic hydrocarbon structure and may further have a substituent, wherein R² is selected from the group consisting of hydrogen, an alkyl group having 1 to 7 carbon atoms, an aryl group having 6 to 14 carbon atoms, a cycloalkyl group having 3 to 10 carbon atoms, an aralkyl group having 7 to 19 carbon atoms, an alkoxyalkyl group having 2 to 11 carbon atoms, a group containing a hetero atom in the carbon skeleton thereof, and a group containing a carbon-carbon unsaturated bond in the carbon skeleton thereof, wherein these groups may be straight or branched, may have an alicyclic hydrocarbon structure and may further have a substituent.

2. An isolated polynucleotide selected from the group consisting of:
   (a) a polynucleotide comprising the nucleotide sequence of SEQ ID NO:4, and
   (b) a polynucleotide that hybridizes with a polynucleotide having a nucleotide sequence complementary to the nucleotide sequence of SEQ ID NO:4 under stringent conditions and encodes a protein which is able to catalyze a reaction in which an α-amino acid of formula (I):

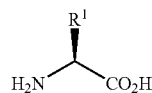   (I)

is reacted with an aldehyde of formula (II):

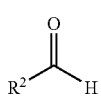   (II)

to form a serine derivative of formula (III):

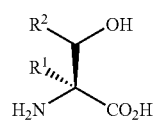   (III)

wherein R¹ is selected from the group consisting of an alkyl group having 1 to 7 carbon atoms, an aryl group having 6 to 14 carbon atoms, a cycloalkyl group having 3 to 10 carbon atoms, an aralkyl group having 7 to 19 carbon atoms, an alkoxyalkyl group having 2 to 11 carbon atoms, a group containing a hetero atom in the carbon skeleton thereof, and a group containing a carbon-carbon unsaturated bond in the carbon skeleton thereof, wherein these groups may be straight or branched, may have an alicyclic hydrocarbon structure and may further have a substituent, wherein R² is selected from the group consisting of hydrogen, an alkyl group having 1 to 7 carbon atoms, an aryl group having 6 to 14 carbon atoms, a cycloalkyl group having 3 to 10 carbon atoms, an aralkyl group having 7 to 19 carbon atoms, an alkoxyalkyl group having 2 to 11 carbon atoms, a group containing a hetero atom in the carbon skeleton thereof, and a group containing a carbon-carbon unsaturated bond in the carbon skeleton thereof, wherein these groups may be straight or branched, may have an alicyclic hydrocarbon structure and may further have a substituent, wherein said stringent conditions comprise washing at a salt concentration corresponding to 1×SSC and 0.1% SDS at 60° C.

3. A cell transformed with the polynucleotide according to claim 1.

4. The cell according to claim 3, wherein the cell is *Escherichia coli*.

5. The polynucleotide according to claim 1, wherein the protein (B) comprises a substitution of the tyrosine located at position 339 with an amino acid selected from the group consisting of serine, histidine, and asaparagine.

6. The polynucleotide according to claim 1, wherein the protein (B) comprises substitution of the asparagine located at position 19 with a serine.

7. A method for producing a serine derivative comprising reacting an α-amino acid of formula (I):

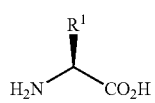
(I)

with an aldehyde of formula (II):

(II)

in a culture comprising the cell according to claim 3 to form the serine derivative of formula (III):

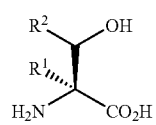
(III)

wherein R¹ is selected from the group consisting of an alkyl group having 1 to 7 carbon atoms, an aryl group having 6 to 14 carbon atoms, a cycloalkyl group having 3 to 10 carbon atoms, aralkyl group having 7 to 19 carbon atoms, alkoxyalkyl group having 2 to 11 carbon atoms, a group containing a hetero atom in the carbon skeleton thereof, and a group containing a carbon-carbon unsaturated bond in the carbon skeleton thereof, wherein these groups may be straight or branched, may have an alicyclic hydrocarbon structure and may further have a substituent, wherein R² is selected from the group consisting of hydrogen, an alkyl group having 1 to 7 carbon atoms, an aryl group having 6 to 14 carbon atoms, a cycloalkyl group having 3 to 10 carbon atoms, an aralkyl group having 7 to 19 carbon atoms, an alkoxyalkyl group having 2 to 11 carbon atoms, a group containing a hetero atom in the carbon skeleton thereof, and a group containing a carbon-carbon unsaturated bond in the carbon skeleton thereof, wherein these groups may be straight or branched, may have an alicyclic hydrocarbon structure and may further have a substituent.

8. The method for producing the serine derivative according to claim 7, wherein the culture further comprises the α-amino acid of formula (I) and the aldehyde of formula (II), and the culture is mixed to form the serine derivative of formula (III).

9. The method for producing the serine derivative according to claim 7, wherein the amino acid of formula (I) is an amino acid selected from the group consisting of phenylalanine, leucine, methionine, alanine, cysteine, tryptophan, isoleucine, cyclohexylalanine, 2-amino-n-butyric acid, 2-aminovaleric acid, 2-aminohexanoic acid, and combinations thereof.

10. The method for producing the serine derivative according to claim 7, wherein the amino acid of formula (I) is α-phenylalanine, and the serine derivative of formula (III) is α-benzylserine.

11. The method for producing the serine derivative according to claim 7, wherein the amino acid of formula (I) is α-leucine, and the serine derivative of formula (III) is α-isobutylserine.

12. The method for producing the serine derivative according to claim 7, wherein the amino acid of formula (I) is α-methionine, and the serine derivative of formula (III) is α-methylthioethylserine.

* * * * *

SEQUENCE LISTING

```
<160> NUMBER OF SEQ ID NOS: 15

<210> SEQ ID NO 1
<211> LENGTH: 23
<212> TYPE: PRT
<213> ORGANISM: Rhodococcus sp.

<400> SEQUENCE: 1

Pro Gly Phe Ser Gln Val Gln Trp Ser Ser Pro Cys Arg Leu Asp Phe
1               5                   10                  15

Arg Asn Glu Gly Arg Val Ala
            20
```

<210> SEQ ID NO 2
<211> LENGTH: 24
<212> TYPE: DNA
<213> ORGANISM: Artificial
<220> FEATURE:
<223> OTHER INFORMATION: primer (SEQA)
<220> FEATURE:
<221> NAME/KEY: misc_feature
<222> LOCATION: (18)..(18)
<223> OTHER INFORMATION: n is a, c, g, or t

<400> SEQUENCE: 2
ccdgghttyw shcargtnca rtgg                                          24

<210> SEQ ID NO 3
<211> LENGTH: 29
<212> TYPE: DNA
<213> ORGANISM: Artificial
<220> FEATURE:
<223> OTHER INFORMATION: primer (SEQB)
<220> FEATURE:
<221> NAME/KEY: misc_feature
<222> LOCATION: (15)..(15)
<223> OTHER INFORMATION: n is a, c, g, or t

<400> SEQUENCE: 3
gghttywshc argtncartg gwshwshcc                                     29

<210> SEQ ID NO 4
<211> LENGTH: 1098
<212> TYPE: DNA
<213> ORGANISM: Rhodococcus sp.
<220> FEATURE:
<221> NAME/KEY: CDS
<222> LOCATION: (1)..(1098)

<400> SEQUENCE: 4

```
atg cca ggc ttt tcg cag gtc cag tgg agt tcg ccg ccc cgg ctc gac      48
Met Pro Gly Phe Ser Gln Val Gln Trp Ser Ser Pro Pro Arg Leu Asp
1               5                   10                  15 ttc cgg aac gag ggg cga gtc gcg ccg acc gag gag atg tgg gag gcc      96
Phe Arg Asn Glu Gly Arg Val Ala Pro Thr Glu Glu Met Trp Glu Ala
                20                  25                  30 atg cgt cgg gca tcc gag aac ttc gag atg tcc tcc ttc ggg acc gat     144
Met Arg Arg Ala Ser Glu Asn Phe Glu Met Ser Ser Phe Gly Thr Asp
            35                  40                  45 ccg agc gtg cgc gaa ctg gaa ctt att ggc gcc gag atg aca ggt cag     192
Pro Ser Val Arg Glu Leu Glu Leu Ile Gly Ala Glu Met Thr Gly Gln
        50                  55                  60 gaa gcc tca tac ttc ttg ccg tcg aca acc gcg gcg acg ttg gtg gcg     240
Glu Ala Ser Tyr Phe Leu Pro Ser Thr Thr Ala Ala Thr Leu Val Ala
65                  70                  75                  80 cta ttg gcg gag gac gtg cgc gca aag caa ctc atc gtc gag gcc agg     288
Leu Leu Ala Glu Asp Val Arg Ala Lys Gln Leu Ile Val Glu Ala Arg
                85                  90                  95 tcg cat ctt tac tgg cta cag cgg ttt cac gac tcg gtg cat gcc ggc     336
Ser His Leu Tyr Trp Leu Gln Arg Phe His Asp Ser Val His Ala Gly
                100                 105                 110 ggg cgc gcc gcc acg atc gag ggc gac aag ttc ggc gtt atg tcg ctg     384
Gly Arg Ala Ala Thr Ile Glu Gly Asp Lys Phe Gly Val Met Ser Leu
            115                 120                 125 agt gac atc gac gag ttg atc aac cgg acc gtt tgg ggc ctt gag aac     432
Ser Asp Ile Asp Glu Leu Ile Asn Arg Thr Val Trp Gly Leu Glu Asn
        130                 135                 140
```

```
cca acg gcc ttc gta tgc ctc gag aac acg cac aac att tgc ggt ggc    480
Pro Thr Ala Phe Val Cys Leu Glu Asn Thr His Asn Ile Cys Gly Gly
145                 150                 155                 160 acc cca ctg tcg gtg gag tac acc agg gaa gcc gct gac atc gcc cga    528
Thr Pro Leu Ser Val Glu Tyr Thr Arg Glu Ala Ala Asp Ile Ala Arg
                165                 170                 175 cgt gca gga gcc aaa ctc ttc atc gat ggc gca cgc atc tgg aat gct    576
Arg Ala Gly Ala Lys Leu Phe Ile Asp Gly Ala Arg Ile Trp Asn Ala
            180                 185                 190 gcc gtc gcg cag gac gtg acc gtg aag gat ctg tgt gaa cct gca gat    624
Ala Val Ala Gln Asp Val Thr Val Lys Asp Leu Cys Glu Pro Ala Asp
        195                 200                 205 gcg gtc gtg ctc tca ctc aac aag gcg ccc atc gca ccg tac ggc gct    672
Ala Val Val Leu Ser Leu Asn Lys Ala Pro Ile Ala Pro Tyr Gly Ala
    210                 215                 220 ctg ctc tgc ggt agc gcg gac atg atc gtg cgt gcc cgc acc gaa gcc    720
Leu Leu Cys Gly Ser Ala Asp Met Ile Val Arg Ala Arg Thr Glu Ala
225                 230                 235                 240 acg cgc atc gga gcc aac cag gtt cac aaa gat ggc atc ttc gcc gct    768
Thr Arg Ile Gly Ala Asn Gln Val His Lys Asp Gly Ile Phe Ala Ala
                245                 250                 255 gcc gcc atc gtc gga ttg aag gac gtc gac cag cga ctg aag gaa gac    816
Ala Ala Ile Val Gly Leu Lys Asp Val Asp Gln Arg Leu Lys Glu Asp
            260                 265                 270 cac cgg cgc gcg cgt cag ctg gcg gag gga ctt tca gct cac cca tcg    864
His Arg Arg Ala Arg Gln Leu Ala Glu Gly Leu Ser Ala His Pro Ser
        275                 280                 285 ctc gat gtc gac gct cga aac acc cga tcc aat ctc gtt cgt atc ggg    912
Leu Asp Val Asp Ala Arg Asn Thr Arg Ser Asn Leu Val Arg Ile Gly
    290                 295                 300 acc tca cgc act ggc gtg agc gcc ctc gag atc gcc gag gaa ctc aaa    960
Thr Ser Arg Thr Gly Val Ser Ala Leu Glu Ile Ala Glu Glu Leu Lys
305                 310                 315                 320 cat caa ggc ctc ggc ttg cag gtg ctt gac cct gac acg ctc agg ctg   1008
His Gln Gly Leu Gly Leu Gln Val Leu Asp Pro Asp Thr Leu Arg Leu
                325                 330                 335 gtc acc tac tgc cgc ata acc gac tgt gac atc gac gaa gct ctc ggg   1056
Val Thr Tyr Cys Arg Ile Thr Asp Cys Asp Ile Asp Glu Ala Leu Gly
            340                 345                 350 att ttc gaa aag gtc gtc tcc aac ctc gtg acg tcc cgc taa           1098
Ile Phe Glu Lys Val Val Ser Asn Leu Val Thr Ser Arg
        355                 360                 365

<210> SEQ ID NO 5
<211> LENGTH: 365
<212> TYPE: PRT
<213> ORGANISM: Rhodococcus sp.

<400> SEQUENCE: 5

Met Pro Gly Phe Ser Gln Val Gln Trp Ser Pro Pro Arg Leu Asp
1               5                   10                  15

Phe Arg Asn Glu Gly Arg Val Ala Pro Thr Glu Glu Met Trp Glu Ala
            20                  25                  30

Met Arg Arg Ala Ser Glu Asn Phe Glu Met Ser Ser Phe Gly Thr Asp
        35                  40                  45

Pro Ser Val Arg Glu Leu Glu Leu Ile Gly Ala Glu Met Thr Gly Gln
    50                  55                  60

Glu Ala Ser Tyr Phe Leu Pro Ser Thr Thr Ala Ala Thr Leu Val Ala
65                  70                  75                  80
```

```
Leu Leu Ala Glu Asp Val Arg Ala Lys Gln Leu Ile Val Glu Ala Arg
                85                  90                  95

Ser His Leu Tyr Trp Leu Gln Arg Phe His Asp Ser Val His Ala Gly
            100                 105                 110

Gly Arg Ala Ala Thr Ile Glu Gly Asp Lys Phe Gly Val Met Ser Leu
            115                 120                 125

Ser Asp Ile Asp Glu Leu Ile Asn Arg Thr Val Trp Gly Leu Glu Asn
    130                 135                 140

Pro Thr Ala Phe Val Cys Leu Glu Asn Thr His Asn Ile Cys Gly Gly
145                 150                 155                 160

Thr Pro Leu Ser Val Glu Tyr Thr Arg Glu Ala Ala Asp Ile Ala Arg
                165                 170                 175

Arg Ala Gly Ala Lys Leu Phe Ile Asp Gly Ala Arg Ile Trp Asn Ala
            180                 185                 190

Ala Val Ala Gln Asp Val Thr Val Lys Asp Leu Cys Glu Pro Ala Asp
            195                 200                 205

Ala Val Val Leu Ser Leu Asn Lys Ala Pro Ile Ala Pro Tyr Gly Ala
        210                 215                 220

Leu Leu Cys Gly Ser Ala Asp Met Ile Val Arg Ala Arg Thr Glu Ala
225                 230                 235                 240

Thr Arg Ile Gly Ala Asn Gln Val His Lys Asp Gly Ile Phe Ala Ala
                245                 250                 255

Ala Ala Ile Val Gly Leu Lys Asp Val Asp Gln Arg Leu Lys Glu Asp
            260                 265                 270

His Arg Arg Ala Arg Gln Leu Ala Glu Gly Leu Ser Ala His Pro Ser
        275                 280                 285

Leu Asp Val Asp Ala Arg Asn Thr Arg Ser Asn Leu Val Arg Ile Gly
    290                 295                 300

Thr Ser Arg Thr Gly Val Ser Ala Leu Glu Ile Ala Glu Glu Leu Lys
305                 310                 315                 320

His Gln Gly Leu Gly Leu Gln Val Leu Asp Pro Asp Thr Leu Arg Leu
                325                 330                 335

Val Thr Tyr Cys Arg Ile Thr Asp Cys Asp Ile Asp Gly Ala Leu Gly
            340                 345                 350

Ile Phe Glu Lys Val Val Ser Asn Leu Val Thr Ser Arg
            355                 360                 365

<210> SEQ ID NO 6
<211> LENGTH: 31
<212> TYPE: DNA
<213> ORGANISM: Artificial
<220> FEATURE:
<223> OTHER INFORMATION: primer (S11F)

<400> SEQUENCE: 6
ggaagttcat atgccaggct tttcgcaggt c                              31

<210> SEQ ID NO 7
<211> LENGTH: 31
<212> TYPE: DNA
<213> ORGANISM: Artificial
<220> FEATURE:
<223> OTHER INFORMATION: primer (S12R)

<400> SEQUENCE: 7
caggatcctt agcgggacgt cacgaggttg g                              31
```

<210> SEQ ID NO 8
<211> LENGTH: 33
<212> TYPE: DNA
<213> ORGANISM: Artificial
<220> FEATURE:
<223> OTHER INFORMATION: Primer (Y339SF)

<400> SEQUENCE: 8
ctcaggctgg tcaccagctg ccgcataacc gac          33

<210> SEQ ID NO 9
<211> LENGTH: 33
<212> TYPE: DNA
<213> ORGANISM: Artificial
<220> FEATURE:
<223> OTHER INFORMATION: Primer (Y339SR)

<400> SEQUENCE: 9
gtcggttatg cggcagctgg tgaccagcct gag          33

<210> SEQ ID NO 10
<211> LENGTH: 33
<212> TYPE: DNA
<213> ORGANISM: Artificial
<220> FEATURE:
<223> OTHER INFORMATION: Primer (Y339HF)

<400> SEQUENCE: 10
ctcaggctgg tcacccattg ccgcataacc gac          33

<210> SEQ ID NO 11
<211> LENGTH: 33
<212> TYPE: DNA
<213> ORGANISM: Artificial
<220> FEATURE:
<223> OTHER INFORMATION: Primer (Y339HR)

<400> SEQUENCE: 11
gtcggttatg cggcaatggg tgaccagcct gag          33

<210> SEQ ID NO 12
<211> LENGTH: 33
<212> TYPE: DNA
<213> ORGANISM: Artificial
<220> FEATURE:
<223> OTHER INFORMATION: Primer (Y339NF)

<400> SEQUENCE: 12
ctcaggctgg tcaccaactg ccgcataacc gac          33

<210> SEQ ID NO 13
<211> LENGTH: 33
<212> TYPE: DNA
<213> ORGANISM: Artificial
<220> FEATURE:
<223> OTHER INFORMATION: Primer (Y339NR)

<400> SEQUENCE: 13
gtcggttatg cggcagttgg tgaccagcct gag          33

<210> SEQ ID NO 14
<211> LENGTH: 33
<212> TYPE: DNA
<213> ORGANISM: Artificial
<220> FEATURE:
<223> OTHER INFORMATION: Primer (N19SF)

```
<400> SEQUENCE: 14
cggctcgact tccggagcga ggggcgagtc gcg                              33

<210> SEQ ID NO 15
<211> LENGTH: 33
<212> TYPE: DNA
<213> ORGANISM: Artificial
<220> FEATURE:
<223> OTHER INFORMATION: Primer (N19SR)

<400> SEQUENCE: 15
cgcgactcgc ccctcgctcc ggaagtcgag ccg                              33
```